United States Patent
Cornelius et al.

(10) Patent No.: US 7,097,643 B2
(45) Date of Patent: Aug. 29, 2006

(54) ELECTRICAL BLOCK POSITIONING DEVICES AND METHODS OF USE THEREFOR

(75) Inventors: Richard Cornelius, Wayzata, MN (US); William Swanson, St. Paul, MN (US)

(73) Assignee: Sinus Rhythm Technologies, Inc., Plymouth, MN (US)

(*) Notice: Subject to any disclaimer, the term of this patent is extended or adjusted under 35 U.S.C. 154(b) by 0 days.

(21) Appl. No.: 10/792,111

(22) Filed: Mar. 2, 2004

(65) Prior Publication Data

US 2004/0215186 A1   Oct. 28, 2004

Related U.S. Application Data

(60) Provisional application No. 60/467,298, filed on May 1, 2003, provisional application No. 60/451,821, filed on Mar. 3, 2003.

(51) Int. Cl.
*A61B 18/18* (2006.01)

(52) U.S. Cl. .................. 606/32; 128/898; 606/41

(58) Field of Classification Search ............ 606/27–52; 128/898
See application file for complete search history.

(56) References Cited

U.S. PATENT DOCUMENTS

| | | |
|---|---|---|
| 4,580,568 A | 4/1986 | Gianturco |
| 5,176,135 A | 1/1993 | Fain et al. |
| 5,234,448 A | 8/1993 | Wholey et al. |
| 5,254,127 A | 10/1993 | Wholey et al. |
| 5,312,456 A | 5/1994 | Reed et al. |
| 5,360,440 A | 11/1994 | Andersen |
| 5,423,851 A | 6/1995 | Samuels |
| 5,507,779 A | 4/1996 | Altman |
| 5,509,924 A | 4/1996 | Paspa et al. |
| 5,531,779 A | 7/1996 | Dahl et al. |
| 5,545,183 A | 8/1996 | Altman |
| 5,551,426 A | 9/1996 | Hummel et al. |
| 5,551,427 A | 9/1996 | Altman |
| 5,569,272 A | 10/1996 | Reed et al. |
| 5,584,879 A | 12/1996 | Reimold et al. |
| 5,618,310 A | 4/1997 | Ger et al. |
| 5,649,906 A | 7/1997 | Gory et al. |
| 5,658,327 A | 8/1997 | Altman et al. |
| 5,662,698 A | 9/1997 | Altman et al. |
| 5,674,272 A | 10/1997 | Bush et al. |
| 5,676,850 A | 10/1997 | Reed et al. |
| 5,713,863 A | 2/1998 | Vigil et al. |
| 5,725,567 A | 3/1998 | Wolff et al. |
| 5,749,890 A | 5/1998 | Shaknovich |

(Continued)

FOREIGN PATENT DOCUMENTS

EP   0 497 620 A2   8/1992

(Continued)

OTHER PUBLICATIONS

*The Thoracic And Cardiovascular Surgeon*, III Supplement, vol. 47, Aug. 1999, pp. 347-351 "An Anatomic Approach To Prevention Of Atrial Fibrillation: Pulmonary Vein Isolation With Through-The-Balloon Ultrasound Ablation ( TTB-USA)".

(Continued)

*Primary Examiner*—Michael Peffley
*Assistant Examiner*—Pete Vrettakos
(74) *Attorney, Agent, or Firm*—Inskeep IP Group, Inc.

(57) ABSTRACT

The present invention provides positioning mechanisms for devices that cause conduction blocks or ablation in desired areas of tissue. The positioning mechanisms allow for variable geometry of the target sites and enable more accurate therapy at the tissue site.

5 Claims, 22 Drawing Sheets

U.S. PATENT DOCUMENTS

| | | | |
|---|---|---|---|
| 5,769,883 | A | 6/1998 | Buscemi et al. |
| 5,824,030 | A | 10/1998 | Yang et al. |
| 5,837,007 | A | 11/1998 | Altman et al. |
| 5,843,169 | A | 12/1998 | Taheri |
| 5,891,108 | A | 4/1999 | Leone et al. |
| 5,899,917 | A | 5/1999 | Edwards et al. |
| 5,910,144 | A | 6/1999 | Hayashi |
| 5,954,761 | A | 9/1999 | Machek et al. |
| 5,980,519 | A * | 11/1999 | Hahnen et al. ............... 606/49 |
| 6,010,531 | A | 1/2000 | Donlon et al. |
| 6,012,457 | A | 1/2000 | Lesh |
| 6,086,582 | A | 7/2000 | Altman et al. |
| 6,102,887 | A | 8/2000 | Altman |
| 6,152,920 | A * | 11/2000 | Thompson et al. ........... 606/41 |
| 6,161,029 | A | 12/2000 | Spreigl et al. |
| 6,179,858 | B1 | 1/2001 | Squire et al. |
| 6,206,914 | B1 | 3/2001 | Soykan et al. |
| 6,210,392 | B1 | 4/2001 | Vigil et al. |
| 6,224,491 | B1 | 5/2001 | Hiromi et al. |
| 6,224,626 | B1 | 5/2001 | Steinke |
| 6,241,726 | B1 | 6/2001 | Raymond Chia et al. |
| 6,254,632 | B1 | 7/2001 | Wu et al. |
| 6,267,776 | B1 | 7/2001 | O'Connell |
| 6,270,476 | B1 | 8/2001 | Santoianni et al. |
| 6,283,992 | B1 | 9/2001 | Hankh et al. |
| 6,293,964 | B1 | 9/2001 | Yadav |
| 6,296,630 | B1 | 10/2001 | Altman et al. |
| 6,305,378 | B1 | 10/2001 | Lesh |
| RE37,463 | E | 12/2001 | Altman |
| 6,346,099 | B1 | 2/2002 | Altman |
| 6,358,247 | B1 | 3/2002 | Altman et al. |
| 6,425,895 | B1 | 7/2002 | Swanson et al. |
| 6,438,427 | B1 | 8/2002 | Rexhausen et al. |
| 6,443,949 | B1 | 9/2002 | Altman |
| 6,500,186 | B1 | 12/2002 | Lafontaine et al. |
| 6,503,247 | B1 | 1/2003 | Swartz et al. |
| 6,514,249 | B1 | 2/2003 | Maguire et al. |
| 6,558,382 | B1 * | 5/2003 | Jahns et al. ................... 606/41 |
| 6,572,652 | B1 | 6/2003 | Shaknovich |
| 6,625,486 | B1 * | 9/2003 | Lundkvist et al. ............ 604/21 |
| 6,702,844 | B1 | 3/2004 | Lazarus |
| 2001/0044619 | A1 | 11/2001 | Altman |
| 2002/0010462 | A1 | 1/2002 | Altman |
| 2002/0019623 | A1 | 2/2002 | Altman et al. |
| 2002/0026228 | A1 | 2/2002 | Schauerte |
| 2002/0026233 | A1 | 2/2002 | Shaknovich |
| 2002/0077691 | A1 | 6/2002 | Nachtigall |
| 2002/0151918 | A1 | 10/2002 | Lafontaine et al. |
| 2003/0069606 | A1 | 4/2003 | Girouard et al. |

FOREIGN PATENT DOCUMENTS

| | | |
|---|---|---|
| EP | 0 558 352 A1 | 9/1993 |
| EP | 0 601 338 A1 | 6/1994 |
| WO | WO 94/07564 A2 | 4/1994 |
| WO | WO 99/55254 A1 | 11/1999 |
| WO | WO 00/36997 A1 | 6/2000 |
| WO | WO 01/19269 A1 | 3/2001 |
| WO | WO 01/26585 A1 | 4/2001 |
| WO | WO 01/26727 A1 | 4/2001 |
| WO | WO 02/00273 A2 | 1/2002 |
| WO | WO 02/24106 A2 | 3/2002 |
| WO | WO 02/071980 A2 | 9/2002 |

OTHER PUBLICATIONS

*The Thoracic And Cardiovascular Surgeon*, III Supplement, vol. 47, Aug. 1999, pp. 352-356 "Catheter Ablation Of Pulmonary Vein Foci For Atrial Fibrillation".

*The New England Journal Of Medicine*, vol. 339, Sep. 3, 1998, pp. 659-666 "Spontaneous Initiation Of Atrial Fibrillation By Ectopic Beats Originating In The Pulmonary Veins".

*European Journal Of Cardio-Thoracic Surgery*, vol. 11, Apr. 4, 1997 (ISSN 1010-7940), pp. 714-721 " Inhibition Of Atrial Fibrillation By Pulmonary Vein Isolation And Auricular Resection—Experimental Study In A Sheep Model".

*Cleveland Clinic Journal Of Medicine*, vol. 53, No. 1, Jan. 2001 (ISSN 0891-1150), "Radiofrequency Ablation Of The Pulmonary Veins: Can It Stop Atrial Fibrillation At Its Source?".

*Journal Of Computer Assisted Tomography*, vol. 25, No. 1, Jan./Feb. 2001, pp. 34-35 "Identification Of Pulmonary Vein Stenosis After Radiofrequency Ablation For Atrial Fibrillation Using MRI".

*Pacing And Clinical Electrophysiology*, Nov. 2000, vol. 23, No. 11, Part II, pp. 1836-1838 Pulmonary Veins—Left Atrial Junction: Anatomic And Histological Study .

* cited by examiner

ELECTRICAL BLOCK POSITIONING DEVICES AND METHODS OF USE THEREFOR

CROSS REFERENCE TO RELATED APPLICATIONS

This application claims the benefit of U.S. Provisional Application No. 60/451,821, entitled Positioning Device For Guiding Device Delivery Or Interventions In Pulmonary Veins Or Other Large Body Vessels, filed Mar. 3, 2003; and U.S. Provisional Application No. 60/467,298, entitled Improved Methods And Devices For Creating Electrical Block At Specific Targeted Sites In Cardiac Tissue, filed May 1, 2003, the entire contents of each being hereby incorporated by reference.

BACKGROUND OF THE INVENTION

Pumping of the human heart is caused by precisely timed cycles of compartmental contractions of the heart muscle which lead to an efficient movement of blood into the heart and out to the various bodily organs and back again to the heart. These precisely timed cycles are controlled and directed by electrical signals that are conducted through the cardiac tissue and can be referred to as pacing signals.

The sinoatrial node (SA node) is the heart's natural pacemaker, located in the upper wall of the right atrium. The SA node spontaneously contracts and generates nerve impulses that travel throughout the heart wall causing both the left and right atriums to sequentially contract according to a normal rhythm for pumping of the heart. These electrical impulses continue to the atrioventricular node (AV node) and down a group of specialized fibers called the His-Purkinje system to the ventricles. This electrical pathway must be exactly followed for proper functioning of the heart.

When the normal sequence of electrical impulses changes or is disrupted, the heart rhythm often becomes abnormal. This condition is generally referred to as an arrhythmia and can take the form of such arrhythmias as tachycardias (abnormally fast heart rate), bradycardias (abnormally slow heart rate) and fibrillations (irregular heart beats).

Of these abnormal heart rhythms, fibrillations, and particularly atrial fibrillations, are gaining more and more attention by clinicians and health workers. Atrial fibrillation develops when a disturbance in the electrical signals causes the two upper atrial chambers of the heart to quiver instead of pump properly. When this happens, the heart is unable to discharge all of the blood from the heart's chambers thus creating a situation where the blood may begin to pool and even clot inside the atrium. Such clotting can be very serious insofar as the clot can break away from the atrial chamber and block an artery in the brain, and thereby cause a stroke in the individual.

A variety of treatments have been developed over the years to treat atrial fibrillation, namely, treatments to either mitigate or eliminate electrical conduction pathways that lead to the arrhythmia. Those treatments include medication, electrical stimulation, surgical procedures and ablation techniques. In this regard, typical pharmacological treatments have been previously disclosed in U.S. Pat. No. 4,673,563 to Berne et al.; U.S. Pat. No. 4,569,801 to Molloy et al.; and also by Hindricks, et al. in "Current Management of Arrhythmias" (1991), the contents of which are herein incorporated by reference.

Surgical procedures, such as the "maze procedure", have also been proposed as alternative treatment methods. The "maze" procedure attempts to relieve atrial arrhythmia by restoring effective atrial systole and sinus node control through a series of incisions.

The maze procedure is an open heart surgical procedure in which incisions are made in both the left and right atrial walls which surround the pulmonary vein ostia and which leave a "maze-like" pathway between the sino-atrial node and the atrio-ventricular node. The incisions are sewn back together but result in a scar line which acts as a barrier to electrical conduction.

Although the "maze" procedure has its advantages, in practice it can be a complicated and a particularly risky procedure to perform since the surgeon is making numerous physical incisions in the heart tissue. Due in part to the risky nature of the maze procedure, alternative, catheter-based treatments have been advanced. Many of these catheter devices create the desired electrical block by way of ablation devices designed to burn lesions into the target tissue. Examples of these devices can be seen in U.S. patents: U.S. Pat. No. 6,254,599 to Lesh; U.S. Pat. No. 5,617,854 to Munsif; U.S. Pat. No. 4,898,591 to Jang et al.; U.S. Pat. No. 5,487,385 to Avitall; and U.S. Pat. No. 5,582,609 to Swanson, all incorporated herein by reference.

Although ablation catheter procedures remain less invasive than previous surgical methods like the "maze" procedure, they nevertheless retain a significant element of risk. For example, ablation procedures often utilize high power RF energy or ultrasonic energy, which may adequately create electrical block, but their inherent destructive nature allows for the possibility of unintended damage to the target tissue or nearby areas.

These techniques are used most often in the left or right atriums by creating electrical block either at discrete sites or along linear paths. Typically, the sites being targeted are referenced from landmarks in the chambers of the heart such as the ostium of the coronary sinus, the pulmonary veins, the tricuspid valve, the mitral valve, and the inferior and superior vena cava.

Currently, commonly used ablation devices are introduced percutaneously and advanced into the right atrium via the vena cava and possibly into the left atrium by a transeptal sheath. The ablation devices are then maneuvered inside the appropriate chamber of the heart by torquing the shaft of the catheter and deflecting the tip to bring the ablation tip in contact with the desired target site.

Positioning these ablation devices accurately is difficult as the atrium is a relatively large chamber, having a highly variable pulmonary vein anatomy which varies from patient to patient. Additionally, the atrium is constantly moving due to the beating of the heart and encounters large volumes of blood moving to and from the pulmonary veins. The blood flow causes difficulty because typical fluoroscopic techniques of injecting dye into the blood flow and allowing this to be carried by the blood to fill and illuminate the desired anatomy require large volume dye injections. Indeed, in most interventional applications, multiple dye injections are needed to periodically check the status of the procedure. This is typically not possible in the pulmonary veins due to the large volume of dye required for each injection and the fact that a patient can only tolerate a limited volume of dye without harming the kidneys.

One technique currently used to guide ablation catheters within this difficult environment involves a Lasso™ circular mapping catheter, manufactured by Biosense Webster which is a Johnson & Johnson company, that places radiopaque mapping electrodes around the perimeter of the ostium of the pulmonary veins. The Lasso™ circular mapping catheter is so named for its distal end, heat-set to curl into a ring or lasso shape. A Lasso™ catheter used for this procedure will typically have the radiopaque electrodes embedded within the lasso segment which allows the ring to be used as a physical and visual guide for an ablation catheter. Typically, the Lasso™ catheter is positioned into the atrium until it seats at the ostium of the pulmonary veins. The radiopaque electrodes act as an atrial ruler for guiding the ablation catheter to ablate around the ostium.

The Lasso™ catheter, however, is not an optimal solution for such ablation procedures since the Lasso™ catheter may be easily pushed into the pulmonary vein, causing the doctor to ablate inside the vein instead of around the ostium. Ablation within the pulmonary vein increases the risk of pulmonary vein stenosis and is therefore typically avoided.

In addition, as previously noted, the geometry of the pulmonary vein ostium is highly variable, often being more oval than round. Such variations can cause the Lasso™ catheter to be improperly positioned, further complicating ablation procedures.

In view of the above, it is apparent that there is a need for a positioning system which can more accurately guide interventions or delivery of devices to the target atrial site (e.g., the ostium of the pulmonary veins) minimizing the need for fluoroscopic dye injections.

OBJECTS AND SUMMARY OF THE INVENTION

It is an object of the present invention to provide an improved position device that can more accurately guide interventions or delivery of devices to the ostium of the pulmonary veins and the atrial walls and thereby provide more accurate ablation procedures.

It is a further object of the present invention to provide an improved catheter that overcomes the drawbacks of the prior art.

The present invention achieves the above stated objects by providing an improved positioning catheter and an improved ablation catheter which is sized and shaped to better conform to the shape of the pulmonary veins.

BRIEF DESCRIPTION OF THE DRAWINGS

FIG. 26b illustrates a top view of the expandable linear ablation device of FIG. 26a;

FIGS. 27a–28e illustrate side views of anchoring pins according to the present invention;

FIG. 28 illustrates a side view of a single needle ablation catheter according to the present invention.

DETAILED DESCRIPTION OF THE INVENTION

Guiding Catheter

The ostium of the pulmonary veins has a highly variable geometry from one patient to another and this presents difficulty in reliably treating atrial arrhythmias using previous ablation methods. To address this problem, guiding or anchoring devices are used to position and secure such ablation devices used to create electrical block.

Figure 1:
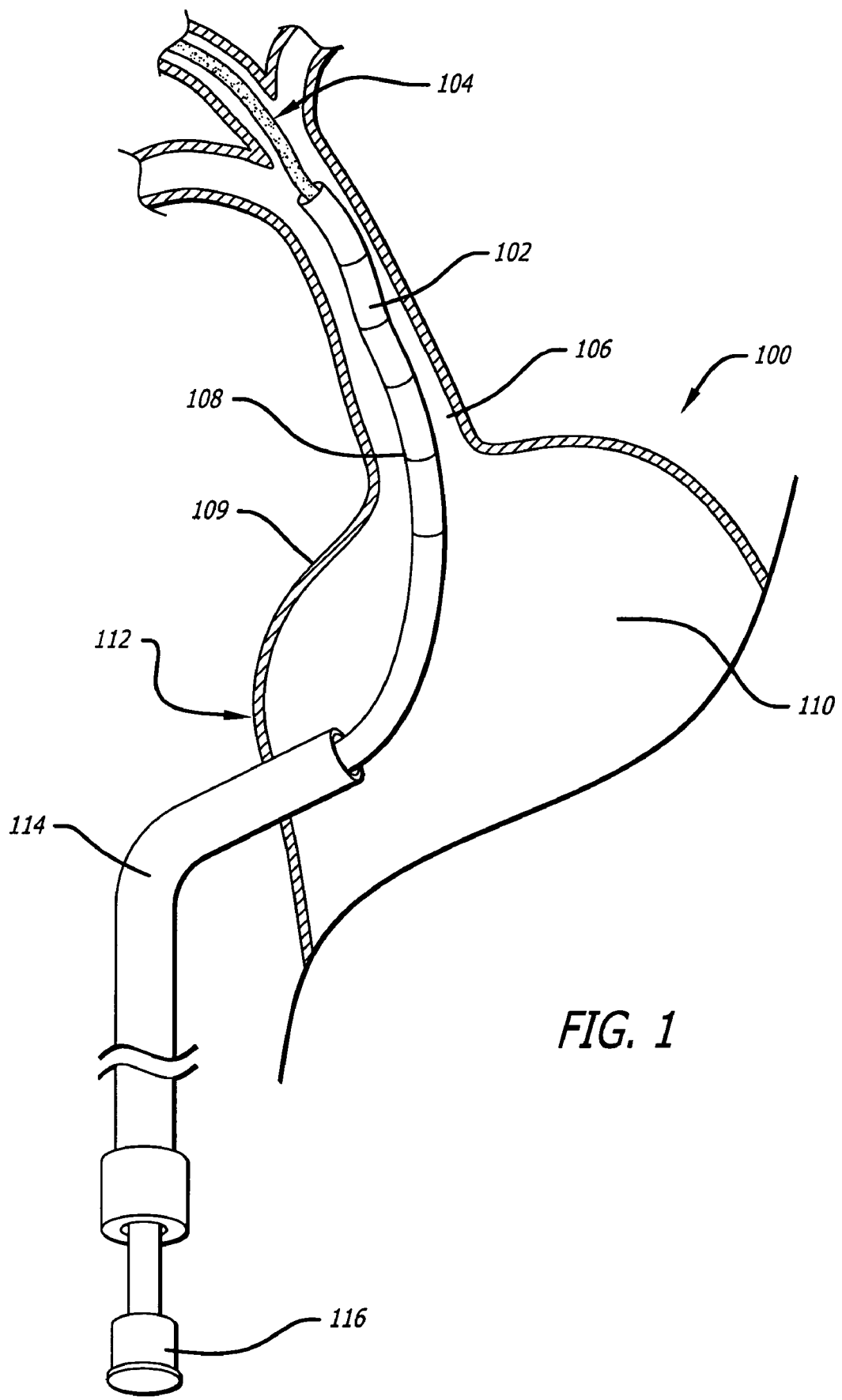
FIG. 1 illustrates a side view of a guiding catheter in according to the present invention.
Figure 2:
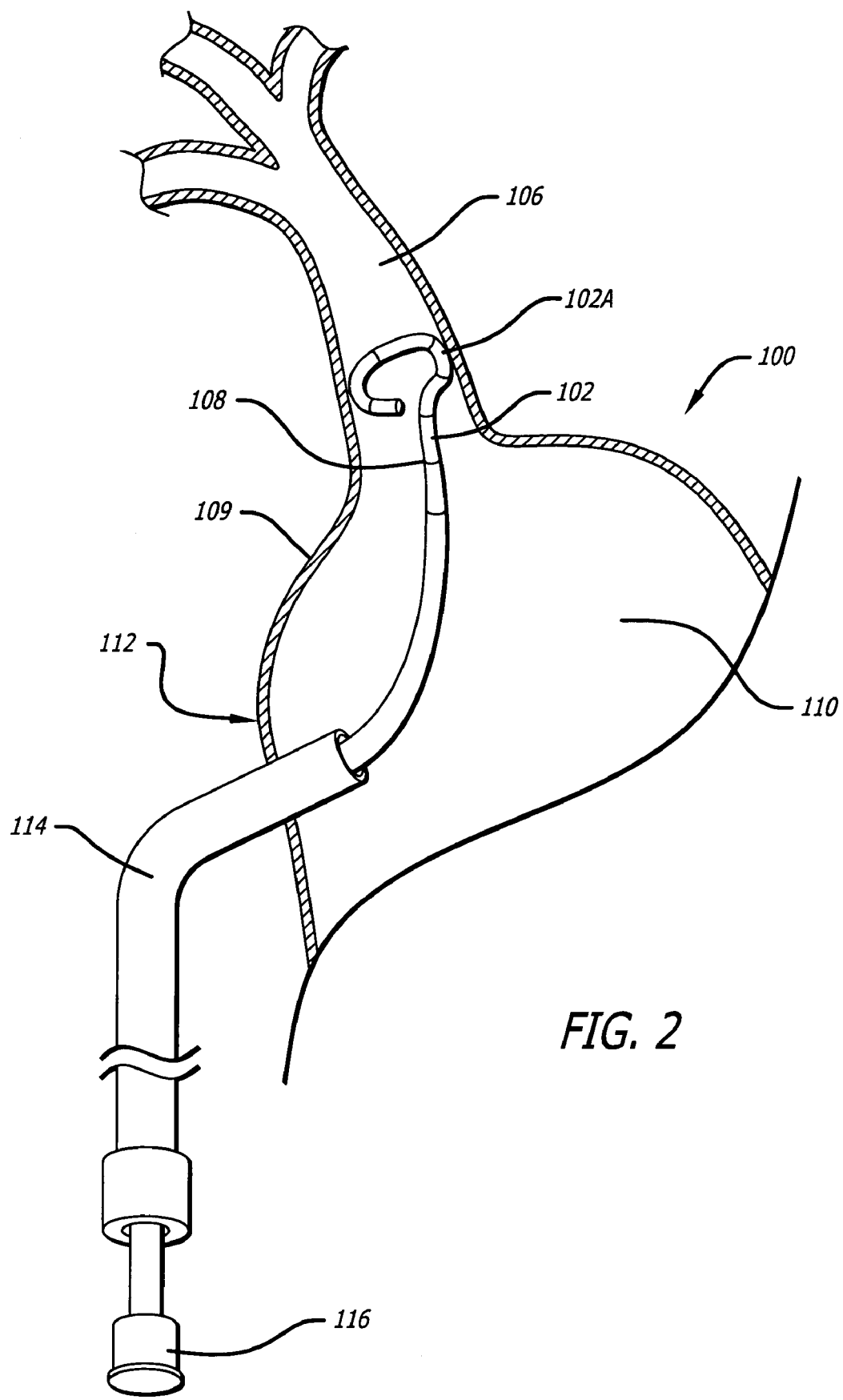
FIG. 2 illustrates a side view of the guiding catheter shown in FIG. 1.
Figure 3:
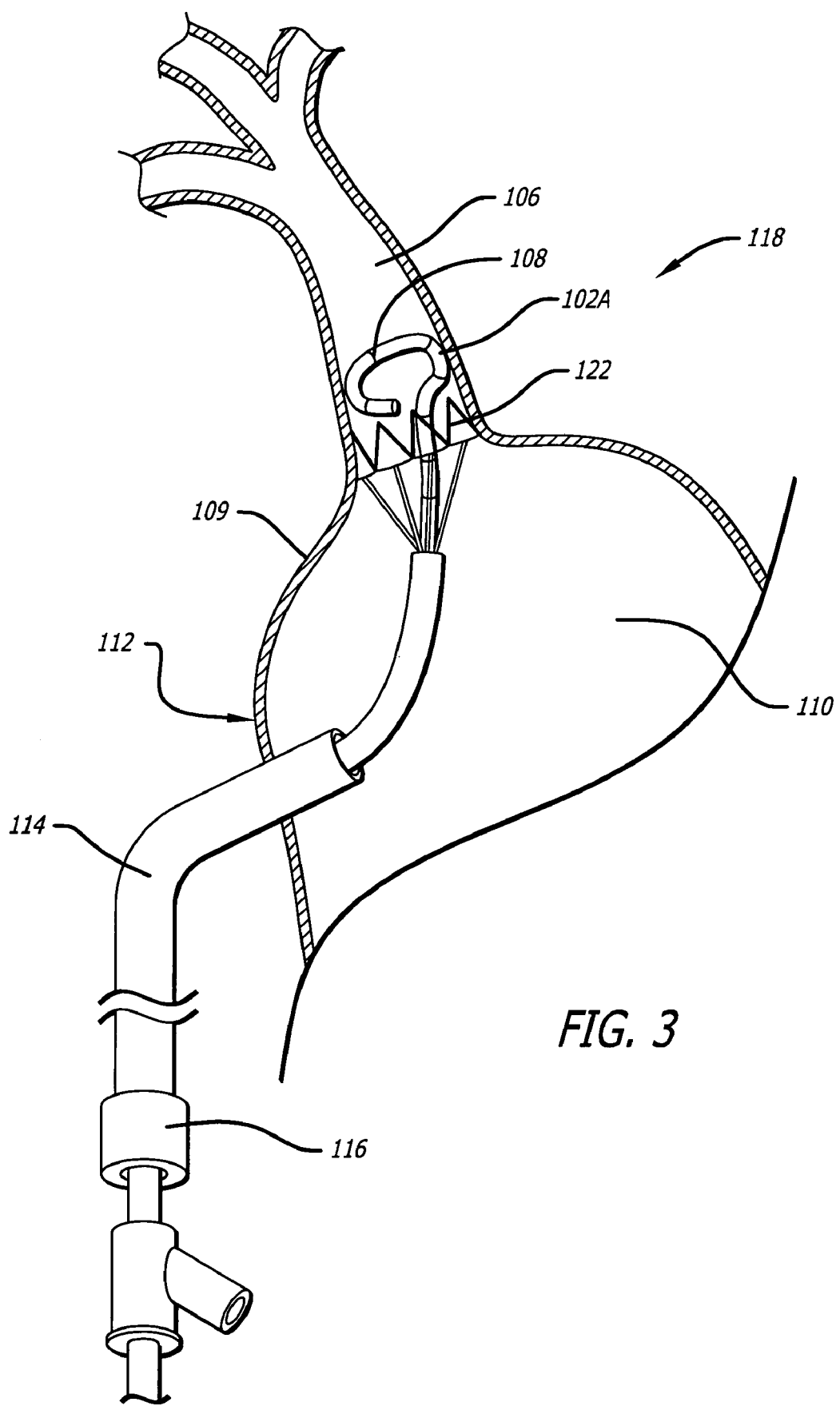
FIG. 3 illustrates a side view of a guiding delivery catheter according to the present invention with an implant delivery catheter tracked over it to the ostium of a pulmonary vein.

One guiding device according to the present invention is a guiding catheter 102, seen in FIGS. 1–3, which may be positioned within the pulmonary veins 106. The guiding catheter 102 has a heat-set distal tip which causes it to self curl into a loop shape 102a, best seen in FIG. 2. Marker rings 108 are spaced along the distal end of the guiding catheter 102 and are typically composed of a radiopaque material that allows visibility during a radio imaging procedure.

As with some percutaneous transeptal procedures, the guiding catheter 102 is deployed through the heart septum 112 and into the left atrium 110 by way of transeptal sheath 114. Such transeptal procedures often involve advancing the transeptal sheath 114 through the vena cava (not shown) and into the right atrium (not shown), where it passes through a surgical incision in the septum 112 to the left atrium 110.

The distal end of the guiding catheter 102 is prevented from curling in FIG. 1 by a guide wire 104 positioned within the guiding catheter 102 and controlled at the proximal end of guide device 100 at access hub 116. Once the guiding catheter 102 is positioned through the ostium 109 and within the pulmonary veins 106, the guide wire 104 may be retracted into the guiding catheter 102, allowing the guiding catheter 102 to curl to a loop shape 102a. Once curled, the guiding catheter 102 will, push against a desired position, such as the inside of a pulmonary vein 106 or the ostium 109 of a pulmonary vein 106.

The marker rings 108 of the catheter extend down along the length of the catheter 102 from the distal ring segment at regular intervals. These markers act as a ruler to locate positions where treatment is desired. The lumen for the guide wire 104 can then be used as a dye injection lumen to get a single image of the pulmonary veins to clearly show the location and size of the ostium 109. This is an advantage over prior art catheters where the markers exist only in the segment of the catheter that self-curls.

The guiding catheter 102 assists in electrical block procedures by guiding a second catheter that has a device 122 to cause ablation of a desired target location as seen in FIG. 3 or by delivering an electrical block implant device. Many ablation catheters are known in the art. These catheters often utilize radio frequency energy, thermal energy, chemical ablation, or mechanical injury, as seen in the exemplary patents U.S. Pat. Nos. 5,720,775, 4,869,248, 5,405,376, and 5,242,441, all of which are herein incorporated by reference.

Implant devices are also used to create electrical block within a heart and can possibly be delivered using the guiding catheter 102. Typically, these devices are placed near the ostium 109 of the pulmonary veins 106 or even within the pulmonary veins 106. Exemplary electrical block devices can be seen in commonly assigned U.S. Patent Application Ser. No. 10/792,110, entitled Electrical Conduction Block Implant Device, filed Mar. 2, 2004, the same filing date as the present application and the contents of which are herein incorporated by reference.

Whether an ablation catheter or an electrical block implant is used for an electrical block procedure, the positioning of the guiding catheter 102 within the heart is critical for a successful procedure. Misalignment of the guiding catheter 102 may lead to ablation of non-target areas within the heart, causing complications. Similarly, a misaligned guiding catheter 102 may deliver an implant to the wrong position which may provide poor or nonexistent electrical block, as well as other complications.

Guiding Catheter with Balloon Segment

As described above, the guiding catheter 102 seen in FIGS. 1–3, creates a friction fit within an area of the heart due to its pre-set diameter that is larger than the diameter of the pulmonary vein 106 or ostium 109. To improve this friction fit, a balloon segment 204 may be included on the end of balloon guiding catheter 200, as seen in FIGS. 4A and 4B.

The balloon guiding catheter 200 is an elongated catheter having a pre-curved distal end and marker rings 202 spaced about the pre-curved distal end as well as down the catheter away from the distal end. Like the guiding catheter 102 discussed previously, the balloon guiding catheter 200 may be positioned transeptally via a transeptal sheath 114 and can be controlled near access hub 116.

Figures 4A, 4B:
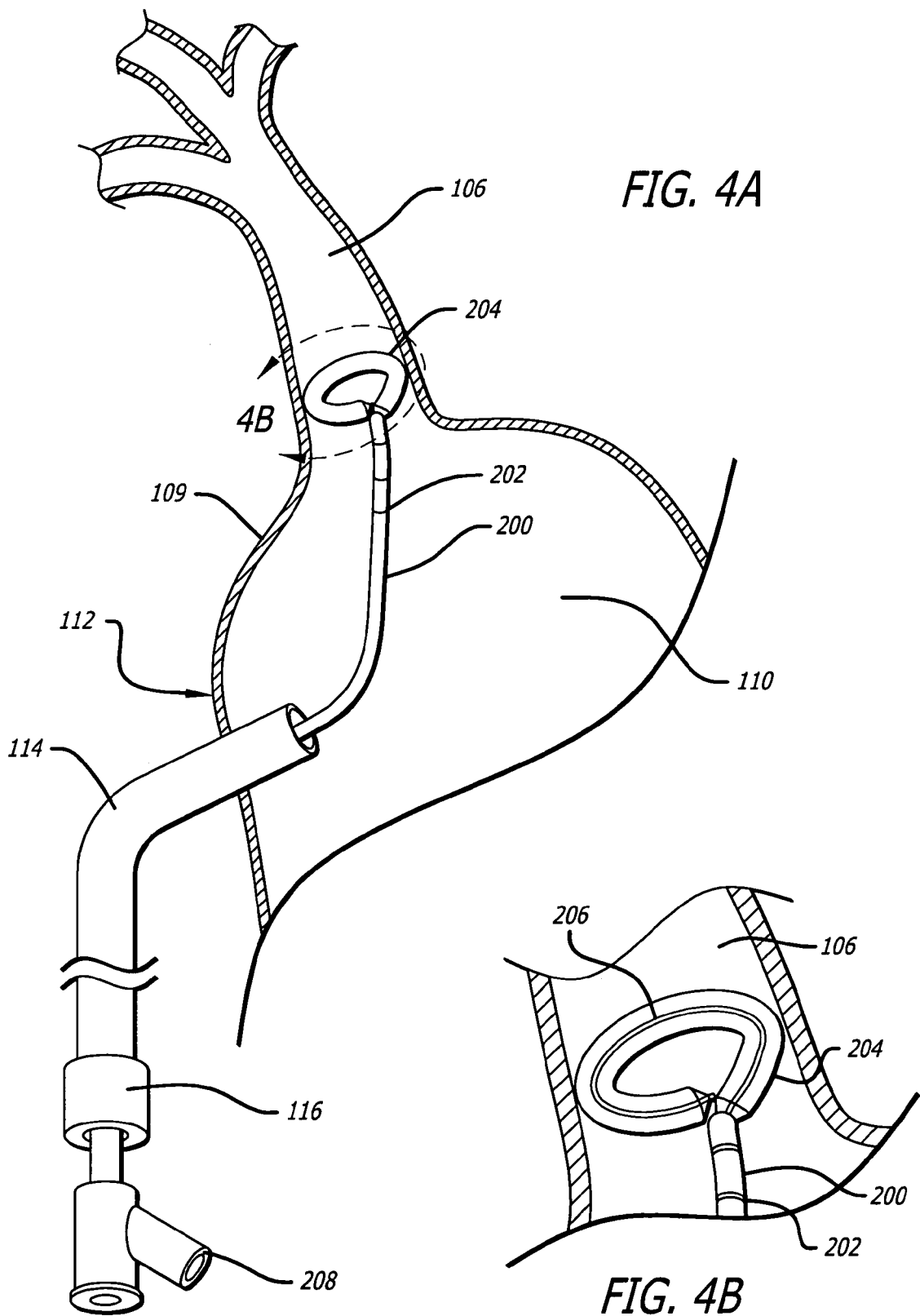
FIG. 4A illustrates a side view of a balloon guiding catheter according to the present invention.
FIG. 4B illustrates a magnified view of the balloon guiding catheter of FIG. 4A.

As shown in FIG. 4B the balloon segment 204 preferably covers the curved section of the distal tip of balloon guiding catheter 200, having an internal wire spine 206 which provides the self curving loop shape. The balloon segment 204 is completely sealed around the wire spine 206, except for a tube (not shown) opening within the balloon segment 204 and passing through the catheter 200 to a media port 208. The media port 208 may be connected to a device which forces pressurized air or liquid into the balloon segment catheter 200, expanding the radial size of the balloon segment 204. The balloon segment 204 may be composed of a durable, pliable, elastic material that allows the balloon segment 204 to cling tightly to the wire spine 206 when deflated, yet expand to many times its original diameter when inflated with media.

In operation, a user positions the balloon guiding catheter 200 within a left atrium 110 via a transeptal sheath 114. As the balloon guiding catheter 200 is withdrawn from the transeptal sheath 114, the balloon segment 204 curls around to a pre-set loop shape. The balloon segment 204 of balloon guiding catheter 200 is positioned at a desired target area, typically within the pulmonary vein 106 or the ostium 109. When the looped balloon segment 204 is positioned at a desired location, the balloon segment is inflated with media via the media port 208. As the balloon segment 204 expands, it presses against the pulmonary vein 106 wall or the ostium 109 wall, providing additional frictional force to anchor the balloon guiding catheter 200.

Guiding Catheter with Tension Wire

Figures 5A, 5B:
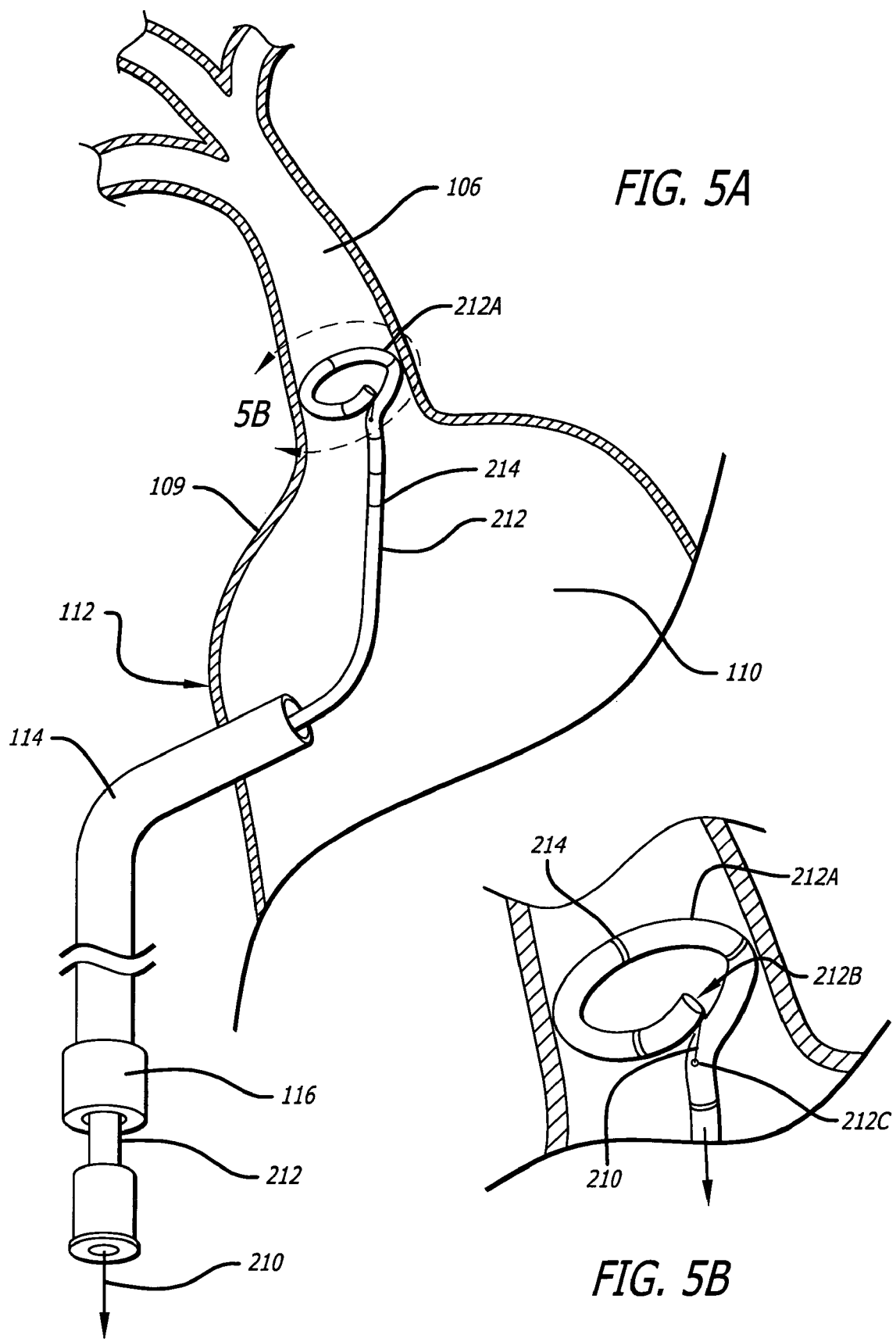
FIG. 5A illustrates a side view of a tension wire guiding catheter according to the present invention.
FIG. 5B illustrates a magnified view of the tension wire guiding catheter of FIG. 5A.

Referring to FIGS. 5A and 5B, a tension wire guiding catheter 212 is illustrated which, when deployed within a target area such as an left atrium, curls around into a loop shape for anchoring purposes. The tension wire guiding catheter 212 differs from prior art devices in that it has a tension wire 210 positioned within a hollow lumen (not shown) of the tension wire guiding catheter 212. The tension wire 210 passes out of wire aperture 212c and is fixed to the distal end 212b of the tension wire guiding catheter 212 while the opposite end of tension wire 210 extends out of access hub 116.

As with previously discussed devices, the tension wire guiding catheter 212 is preferably deployed to a target area such as the left atrium via the transeptal sheath 114. Within the sheath, the tension wire guiding catheter 212 remains relatively straight, with the exposed tension wire 210 in a loose, non-taught position at the distal tip. Preferably, the distal tip of tension wire guiding catheter 212 does not have a pre-set curve, however, a pre-set may be used to assist in creating a desired loop 212a conformation.

As the tension wire guiding catheter 212 is withdrawn from the transeptal sheath 114, the user increases tension on the tension wire 210 by pulling on the tension wire 210 at the proximal end, near the access hub 116. As the tension on the tension wire 210 increases, the distal tip of the tension wire guiding catheter 212 bends around into a loop 212a. In this manner, the user can adjust the diameter of the loop 212a by increasing or decreasing the tension applied at the proximal end of the tension wire 210. With such a variable diameter loop 212a, the outward pressure of the loop 212a against the anchor area (i.e. the pulmonary vein 106 or ostium 109) can be adjusted and thus increased to better secure the tension wire guiding catheter 212 in place.

Guiding Catheter with Anchoring Pins

Figure 6:
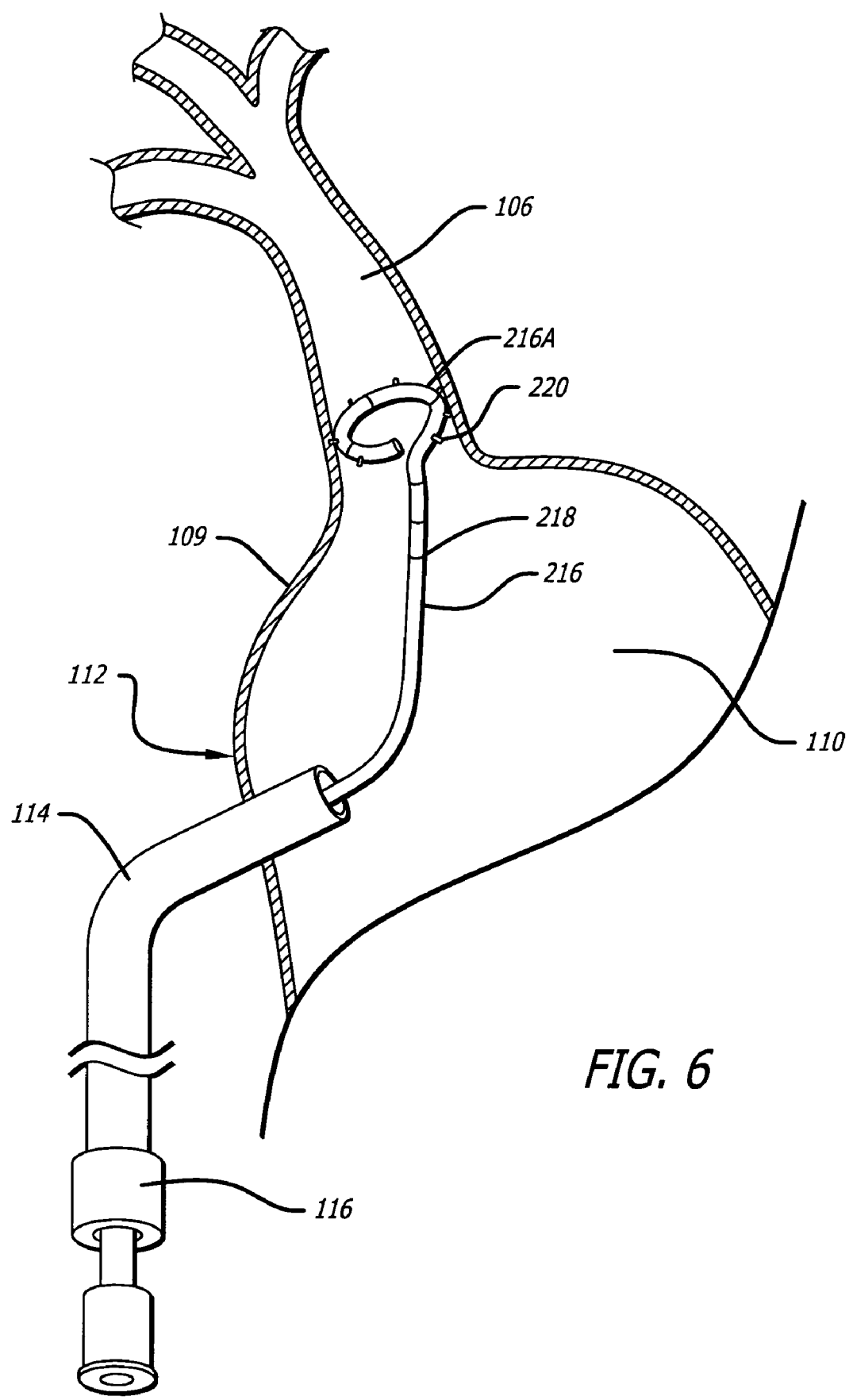
FIG. 6 illustrates a side view of a guiding catheter with anchoring pins according to the present invention.

Referring now to FIG. 6, yet another preferred embodiment of the present invention is illustrated. The anchoring pin guiding catheter 216 provides additional anchoring support by providing a plurality of anchoring pins 220 along the distal end of the anchoring pin guiding catheter 216.

The overall shape of anchoring pin guiding catheter 216 is similar to that of previously discussed guiding catheters, in that it has an elongated shape, sized to fit within the transeptal sheath 114, marker rings 218 preferably composed of a radiopaque compound and which extend along the curved distal tip and downwardly along the catheter, and a pre-set distal tip that naturally conforms to a loop shape 216a.

Anchoring pin guiding catheter 216 differs from prior designs by including multiple anchoring pins 220, preferably positioned on the distal end of anchoring pin guiding catheter 216, so as to extend radially outward from the loop 216a. These anchoring pins 220 may be simple sharp points, barbs, or other similar designs capable of at least partially penetrating cardiac or vein tissue. In addition, the anchoring pins 220 are sized so as to fit within transeptal sheath 114, allowing the anchoring pin guiding catheter 216 to slide unhindered.

In operation, a user operates the anchoring pin guiding catheter 216 in a manner similar to previous designs, beginning by preferably accessing the left atrium by way of a transeptal procedure. Once the transeptal sheath 112 is positioned within the septum 112, the anchoring pin guiding catheter 216 is withdrawn from the transeptal sheath 114, causing the distal tip of the catheter 216 to curl around to its natural state, forming a loop 216a with anchoring pins 220 projecting radially away from the loop's 216a center. The loop 216a is then positioned at a desired anchoring target, such as within a pulmonary vein 106 or the ostium 109, causing the loop 216 and consequently the anchoring pins 220 to wedge into the anchoring tissue. In this manner, the anchoring pin guiding catheter 216 maximizes the standard anchoring support of the typical loop 216a with the anchoring pins 220.

Elongated Friction Catheter

Figure 7:
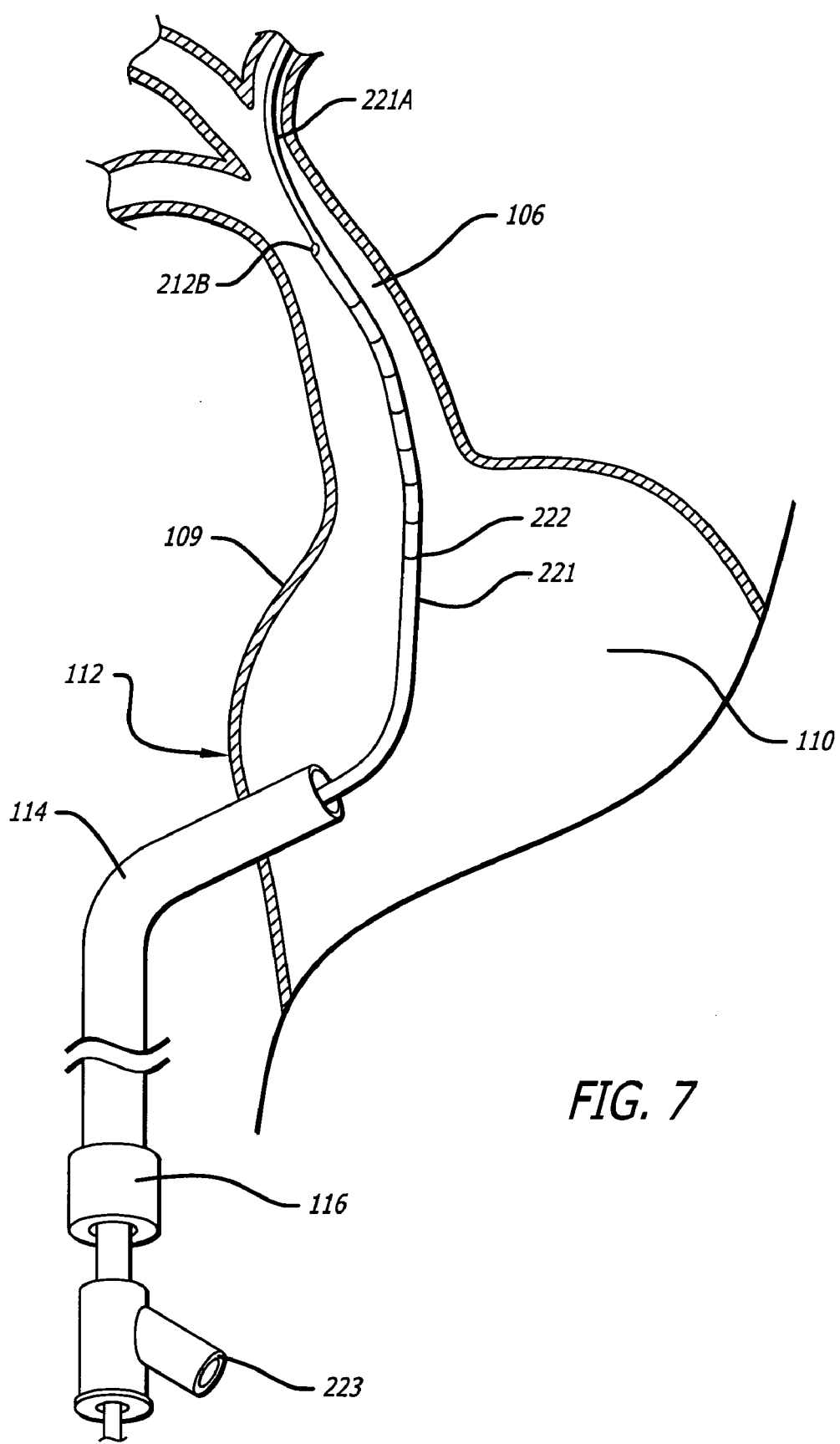
FIG. 7 illustrates a side view of a friction catheter according to the present invention.

In another preferred embodiment of the present invention, best seen in FIG. 7, the anchoring force is achieved by a friction catheter 221 having a soft, elongated distal end 221a, lacking a pre-set curve or loop shape. Instead of creating radial force against the walls of a pulmonary vein as other anchoring catheters do (e.g. the previous guiding catheter embodiments described in this application), the present preferred embodiment employs cumulative friction along the path of the elongated distal end 221a, similar to a coronary guide wire.

Preferably, the cumulative friction is maximized by positioning the elongated distal end 221a of the friction catheter 221 to a more distal location within the pulmonary veins 106. The branches and curves of the pulmonary veins 106 press against various areas of the elongated distal end 221a, creating friction along the path of the elongated distal end 221a.

As with the embodiments described elsewhere in this application, the friction catheter 221 has marker rings 222 spaced along its axial length, an access hub 116 for controlling and manipulating the friction catheter 221, and a transeptal sheath 114 for delivering the friction catheter 221 through the heart septum, into the left atrium.

An additional lumen (not shown) may be included within the friction catheter 221 for providing contrast during a procedure. A supply of contrast (typically fluoroscopic dye) may be introduced into the inner contrast lumen via contrast inlet port 223. Under pressure, the contrast travels through the lumen of the fiction catheter 221, exiting through exit port 221b. Exit port 221b is simply an aperture within the friction catheter 221 sidewall, just distal to the marker rings 222. In this manner, the friction catheter 221 delivers contrast dye to a desired target area during a procedure.

The anchoring force of the friction catheter 221 can be increased by creating additional friction within the pulmonary vein 106. For example, friction may be created by increasing the length, flexibility, or material of the elongated distal end 221a.

Figure 8:
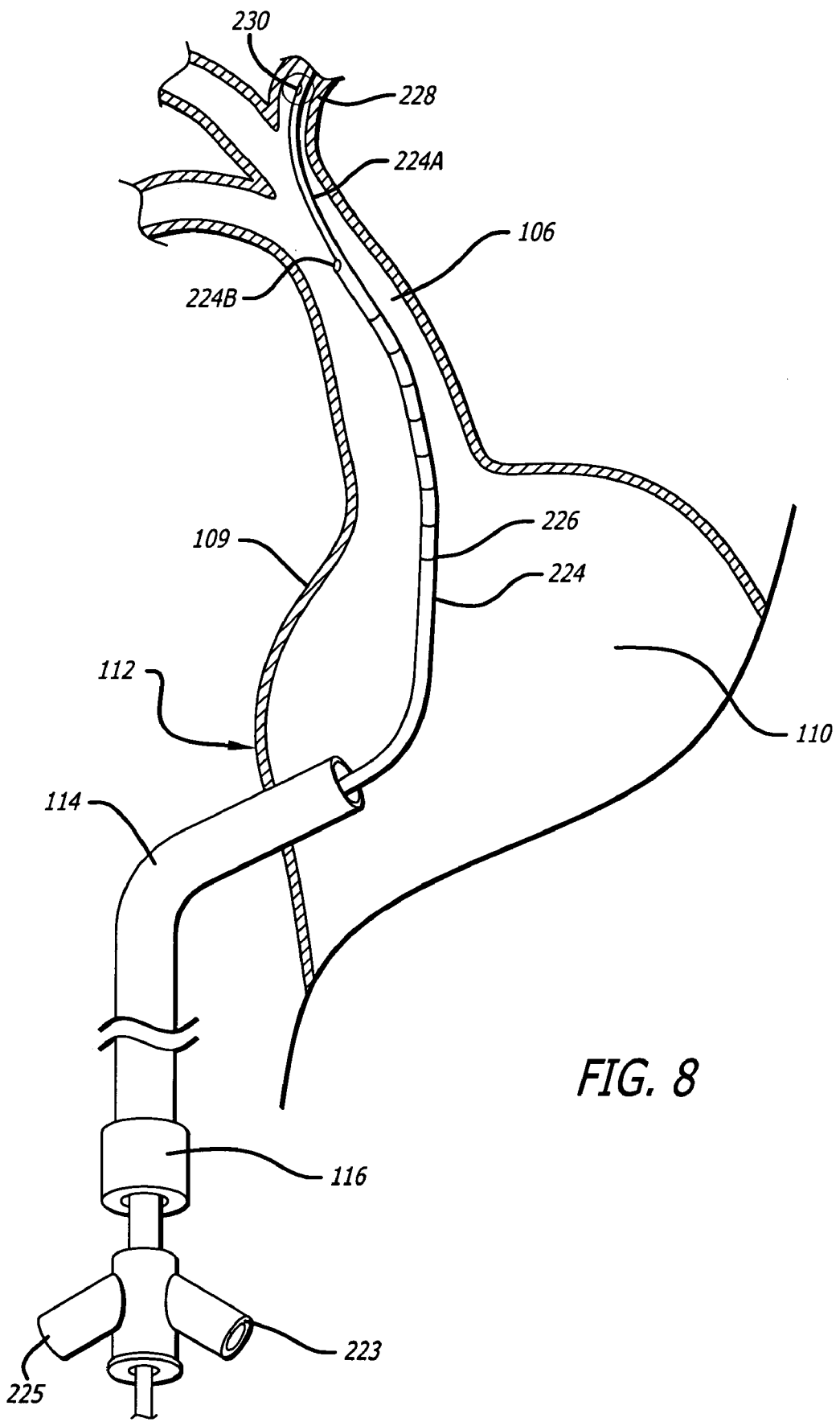
FIG. 8 illustrates a side view of a friction catheter with anchoring balloon according to the present invention.

Referring to FIG. 8, the anchoring ability of the friction catheter 224 may be further enhanced with the addition of an anchoring balloon 228 which can be inflated to press against the walls of the pulmonary vein 106.

The balloon friction catheter 224 has an additional media lumen (not shown), allowing a pressurized media supply such as saline or contrast to be connected to the media lumen via media inlet 225. Once within the media lumen, the media moves along the length of the balloon friction catheter 224 until it reaches inflation port 230, located at the distal tip, within the balloon 228. The media then fills the balloon 228, which expands to a desired size to press against the walls of the pulmonary vein 106.

As with the previously mentioned friction catheter 221, the balloon friction catheter 224 may include a contrast lumen (not shown) and a contrast outlet port 224b for providing contrast media for imaging purposes during the procedure. Additionally, marker rings 224 may be positioned proximal to the elongated distal end 224a, for further visual reference during a procedure.

Anchoring Cage Catheter

Referring now to FIGS. 9A, 9B, 10A, and 10B, a preferred embodiment according to the present invention is illustrated having an expanding anchoring cage 236 or 240. The anchoring cage catheter 230 creates anchoring force with a cage-like section that can expand to a greater diameter once positioned in a desired target location within a pulmonary vein 106.

Figures 9A, 9B:
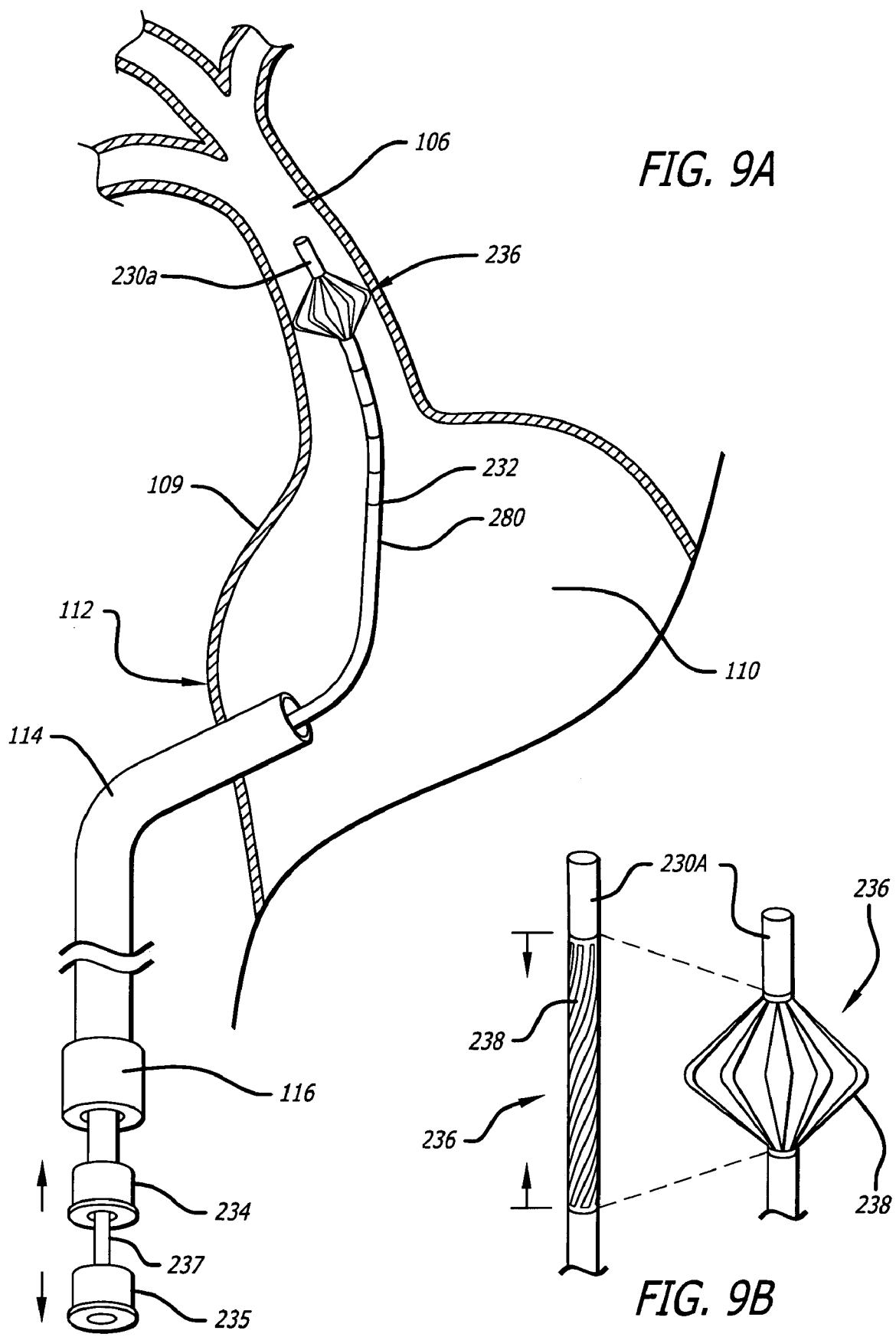
FIG. 9A illustrates a side view of an anchoring cage catheter according to the present invention.
FIG. 9B illustrates a magnified view of the anchoring cage catheter of FIG. 9A.

FIGS. 9A, 9B show an anchoring cage catheter 230 having an anchoring cage 236 composed of deformable strips 238. These deformable strips 238 may be composed of metal, plastic, or other material that will allow each strip to bend without creasing or breaking.

The anchoring cage 236 is located distal to the marker rings 232 to facilitate positioning within the pulmonary vein 106. An inner control rod 237 is located within anchoring cage catheter 230, and is fixed to distal tip 230a. At the proximal end of the anchoring cage catheter 230 are catheter handle 234 (fixed to the anchoring cage catheter 230) and control rod handle 235 (fixed to the control rod 237), which allow a user to move the control rod 237 relative to the anchoring cage catheter 230.

Since the control rod 237 is fixed to the distal catheter end 230, pulling the control rod 237 proximally relative to the anchoring cage catheter 230 moves the distal catheter tip 230a in a proximal direction, expanding the deformable strips 238 of the anchoring cage 236. Thus, a user can expand the anchoring cage 236 to press against the walls of the pulmonary veins 106, providing anchoring force to maintain a desired position of the anchoring cage catheter 230.

Figures 10A, 10B:
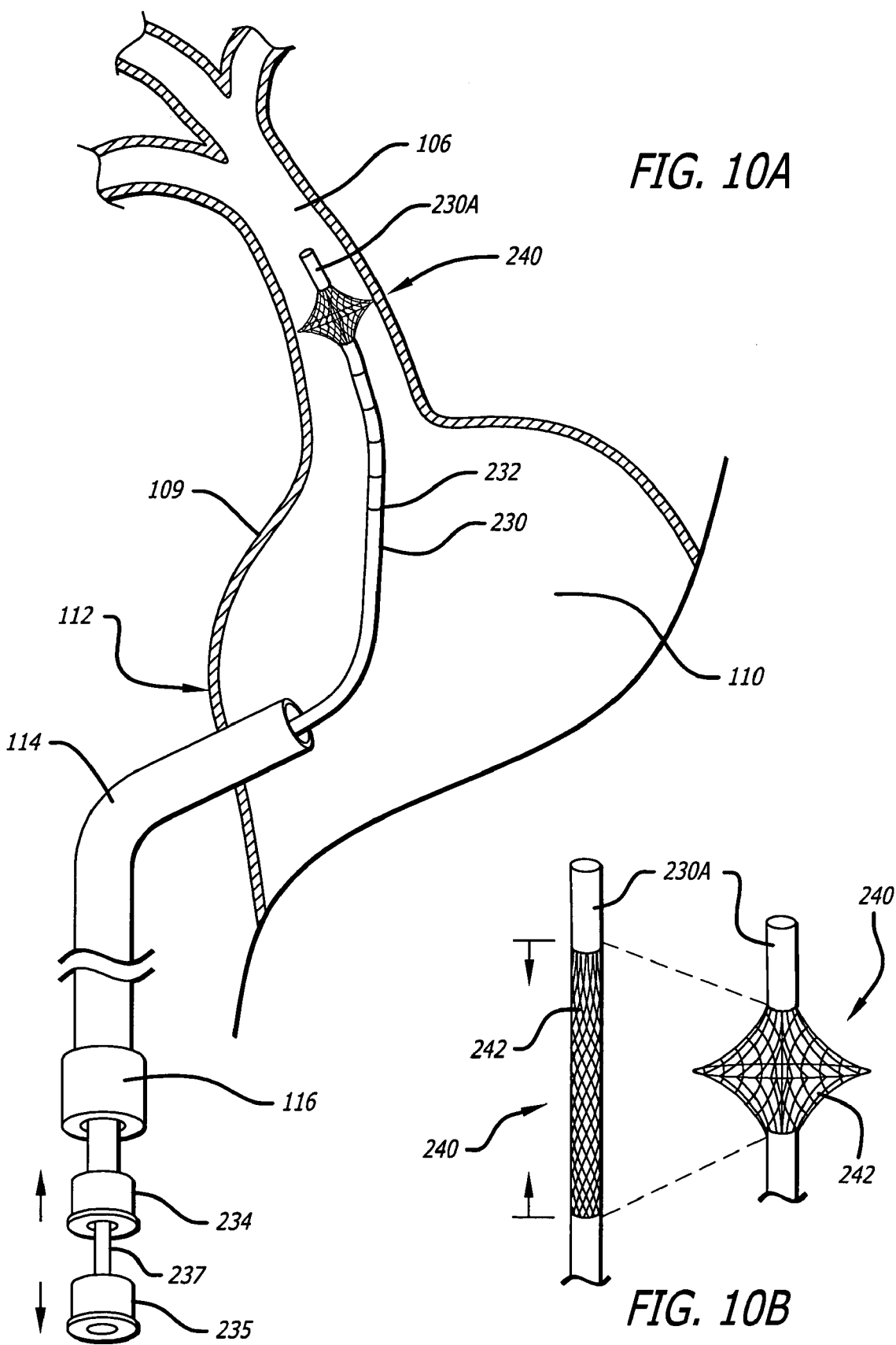
FIG. 10A illustrates a side view of another anchoring cage catheter according to the present invention.
FIG. 10B illustrates a magnified view of the anchoring cage catheter of FIG. 10A.

FIGS. 10A and 10B illustrate a similar preferred embodiment of an anchoring cage catheter 230, having an anchoring cage 240 which can be expanded in diameter by the control rod 237. However, instead of the deformable strips 238 of anchoring cage 236, anchoring cage 240 is composed of deformable mesh 242. The deformable mesh 242 can be composed of metal, plastic or any other material which will allow it to flex without creasing or breaking.

By pulling the control rod 237 proximally relative to the anchoring cage catheter 240 moves the distal catheter tip 230a in a proximal direction, expanding the deformable mesh 242 of the anchoring cage 240. Thus, a user can expand the anchoring cage 240 to press against the walls of the pulmonary veins 106, providing anchoring force to maintain a desired position of the anchoring cage catheter 240.

Mesh Anchoring Ball Catheter

Referring now to FIGS. 11–14, a preferred embodiment of a mesh anchoring catheter 250 is shown according to the present invention, having an expandable mesh section 252 which can conform to, and press against the inner wall of a pulmonary vein 106.

The expandable mesh section 252 is composed of an open mesh preferably made of metal, plastic, or other flexible material, which allows blood to flow therethrough. This mesh also conforms to the shape of the target anchor area, such as an ostium or pulmonary vein 106. It is common for some ostia to be oval in shape, rather than circular, yet in these cases the expandable mesh section 252 is capable of conforming to such an oval shape and anchor the mesh anchoring catheter 250.

Figure 11:
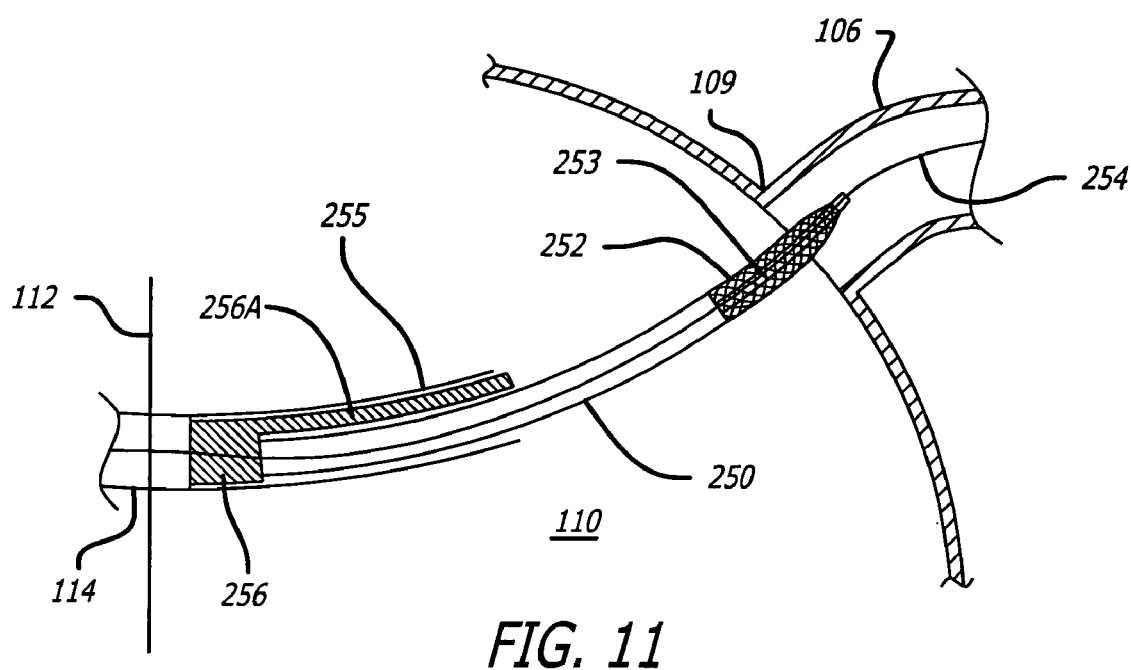
FIG. 11 illustrates a side view of a mesh anchoring ball catheter according to the present invention.

The distal mesh section 252 is initially unexpanded during transeptal delivery to the left atrium (see FIG. 11). An inner control shaft 253 within the mesh anchoring catheter 250 controls the expansion by fixing to the distal end of mesh section 252. Since the proximal end of the mesh section 252 is fixed to the mesh anchoring catheter 250 body, a user can pull on the inner control shaft 253 relative to the mesh anchoring catheter 250, moving the distal end of mesh section 252 closer to the proximal end, thus forcing the mesh section 252 outward into a ball shape seen best in FIGS. 12–14.

As mentioned earlier, such catheter designs serve as both anchoring devices and guide mechanisms for treatment catheters and devices such as ablation catheters. Referring once more to FIGS. 11–14, an ablation catheter 256 having an elongated ablating arm can be seen which advances over the mesh anchoring catheter 250. The elongated arm 256a of ablation catheter 256 has a gradual pre-set curve away from the mesh anchoring catheter 250, due to an elastic, preconfigured, nitinol core.

As seen in FIG. 11, the ablation catheter 256 is positioned within a deployment sheath 255 which prevents the arm of ablation catheter 256 from curving outward, thus allowing both the deployment sheath 255 and the ablation catheter 256 to slide within transeptal sheath 114.

Figure 12:
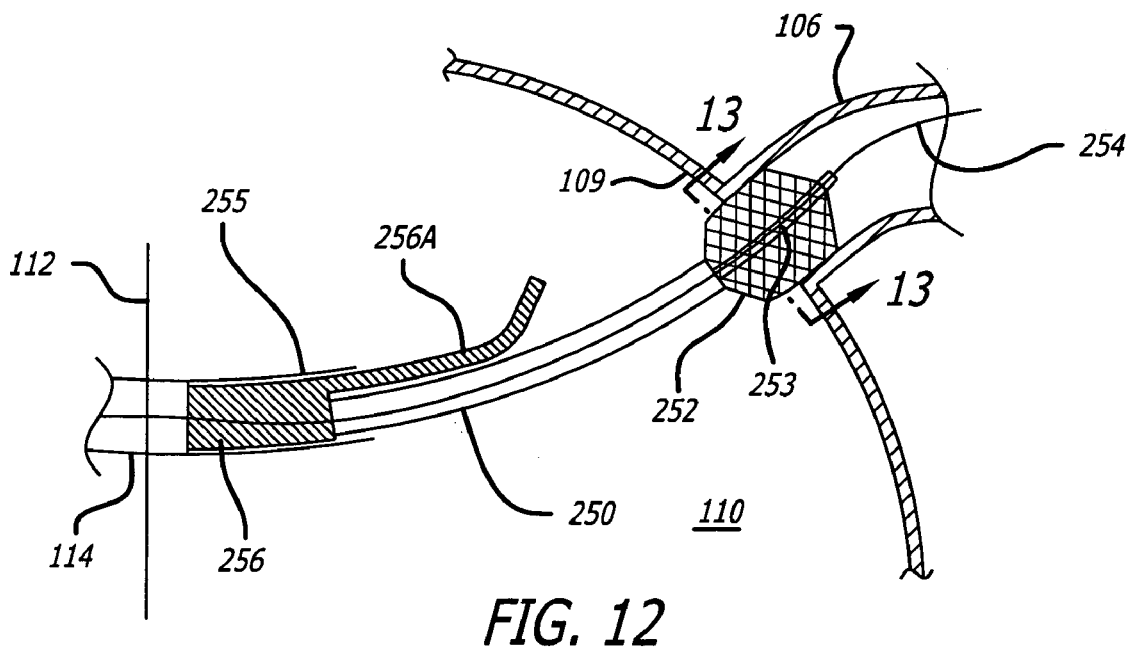
FIG. 12 illustrates a side view of the mesh anchoring ball catheter of FIG. 11.
Figure 13:
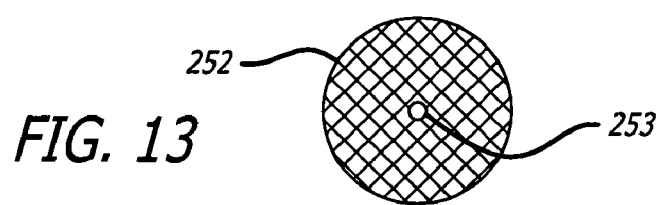
FIG. 13 illustrates a view along view lines 13.

When the mesh anchoring catheter 250 has been positioned, with assistance of the distal guide wire 254, and anchored at a desired location, for example within the pulmonary vein 106, the deployment sheath 255 is pulled back relative to the ablation catheter 256 as seen in FIG. 12. With nothing to restrict it, the ablation arm of ablation catheter 256 moves outward, away from the mesh anchoring catheter 250 body.

Figure 14:
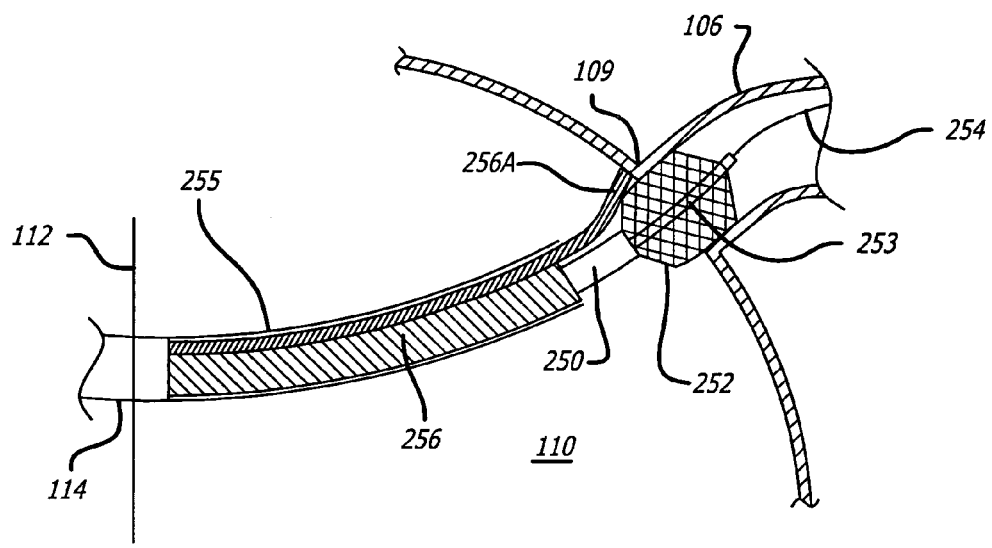
FIG. 14 illustrates a side view of the mesh anchoring ball catheter of FIG. 11.

Referring to FIG. 14, the ablation catheter 256 is advanced distally, toward the mesh section 252 of mesh anchoring catheter 252. Since the mesh section 252 is in its expanded ball shape, the arm of ablation catheter 256 is further deflected away from the mesh anchoring catheter 250, allowing the tip of ablation catheter 256 to contact a desired target area around the ostia 109 of the pulmonary vein 106.

The ablation catheter 256 enables the treatment of a focal site defined by the ball-shaped mesh section 252 seated within the pulmonary vein 106. Additional target electrical block sites can be treated with this device by rotating the mechanism to any additional desired sites around the ball-shaped mesh section 252. Since the ball-shaped mesh section 252 will conform to a non-round ostium and the treatment mechanism defines its position off of the surface of the mesh section 252, these sites can be reached and treated reliably around the perimeter of the ostium 109, if so desired. If it is desired to create a full line of electrical block around the ostium 109, then the device could also have multiple treatment arms located around the mesh anchoring catheter 250 to allow multiple points to be treated simultaneously, minimizing the need to rotate the shaft to create a full line around the ostium 109.

A handle (not shown) may be provided at the proximal end of the ablation catheter 256 for facilitating ablation catheter 256 rotation. Additionally, this handle may be indexed to allow greater rotational control of the rotation of the ablation catheter 256, and thus the areas where electrical block is created.

The ablation catheter 256 of this preferred embodiment, as well as any of the other embodiments of the present invention, may use a variety of ablation techniques, such as radio frequency, microwave, cryogenic or similar previously disclosed energy sources. Further, the tip of the ablation catheter 256 arm may include a small infusion or needle tip for delivery of a chemical or drug such as an alcohol which would create an injury to the target tissue. The ablation catheter 256 arm tip could also include a delivery mechanism to apply an implant such as a staple to create the desired the desired electrical block, as described in PCT Publication No. WO 03/003948, hereby incorporated by reference.

Figure 15:
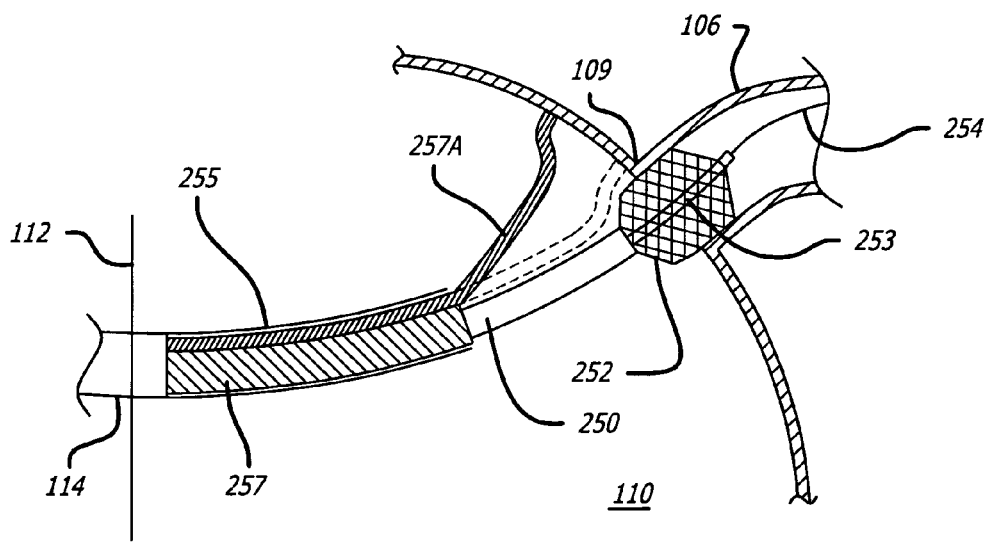
FIG. 15 illustrates a side view of a mesh anchoring ball catheter according to the present invention.

As seen in FIG. 15, different target areas may be reached by the ablation catheter with elongated arm 257. The ablation catheter with elongated arm 257 is similar to the previous embodiment, having a pre-set curved shape which when unconstrained results in the tip of the elongated arm 257a contacting the tissue of the target location spaced radially out from the ball shaped mesh section 252. However, the elongated arm 257a is longer than the previously discussed embodiment, allowing the arm 257a to move outward to a radial diameter of about 4 cm.

This elongated arm 257a allows a user to ablate target sites a greater distance in diameter from the mesh anchoring catheter 250, due to its increased length. The outward curve of the elongated arm 257a can be varied by the deployment sheath 255, which can be adjusted relative to the ablation catheter 257 to cover proximal portions of the elongated arm 257a, thus varying the degree the elongated arm 257a bends outward. In this manner, a user controls the diameter and rotational position of where the ablation is to occur. By controlling this radial position of the elongated ablation arm, it is possible to create linear lesion radially out from the mesh.

Figure 16:
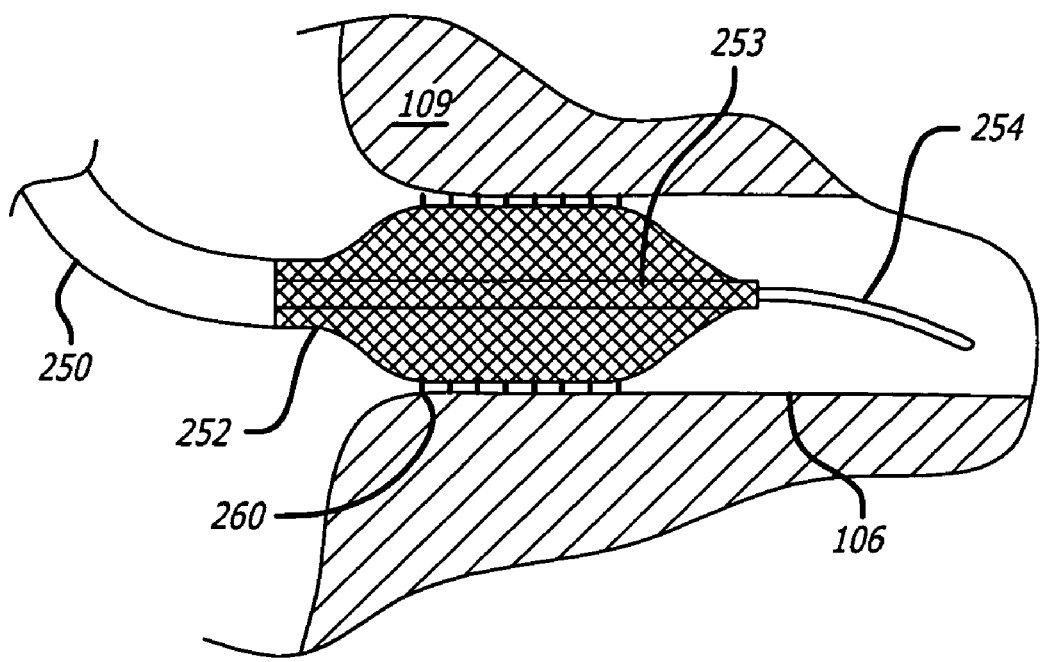
FIG. 16 illustrates a side view of a mesh anchoring ball catheter according to the present invention.

FIG. 16 illustrates yet another preferred embodiment of the mesh anchoring catheter 250, having ablation pins 260 positioned around the circumference of the expanded, ball-shape mesh section 252 for causing electrical block inducing injury to the ostium 109 of the pulmonary vein 106. Ablation pins 260 may be needle shaped, barbed or any other injury-causing pin shape. Other pin shape examples may be seen in the commonly owned U.S. provisional patent application No. 60/467,298, entitled Improved Methods And Devices For Creating Electrical Block At Specific Targeted Sites In Cardiac Tissue, the contents of which are hereby incorporated by reference.

In another preferred embodiment (not shown), additional radiopaque marker bands can be mounted around the perimeter of the expanded ball-shaped mesh section 252 (described above) to visually assist a user during a procedure.

In another preferred embodiment (not shown), the expanded ball-shaped mesh section 252 (described above) may have electrocardiogram (EKG) leads located at varying positions around the circumference of the mesh section 252. These EKG leads maybe connected through wiring within the mesh anchoring catheter 250, and out to a monitoring device, allowing a user to further map the perimeter of the ostium 109 to guide the location of the treatment mechanism.

In yet another preferred embodiment (not shown), the previously described mesh section 252 of mesh anchoring catheter 250 may be replaced with a low pressure balloon having a perfusion lumen to prevent blood occlusion at the ostium 109. In this manner, the low pressure balloon expands against the ostium of the pulmonary vein, allowing the ablation pins or other ablation devices to create electrical block in a target area.

Catheter with Opposing Treatment Arms

Figure 17:
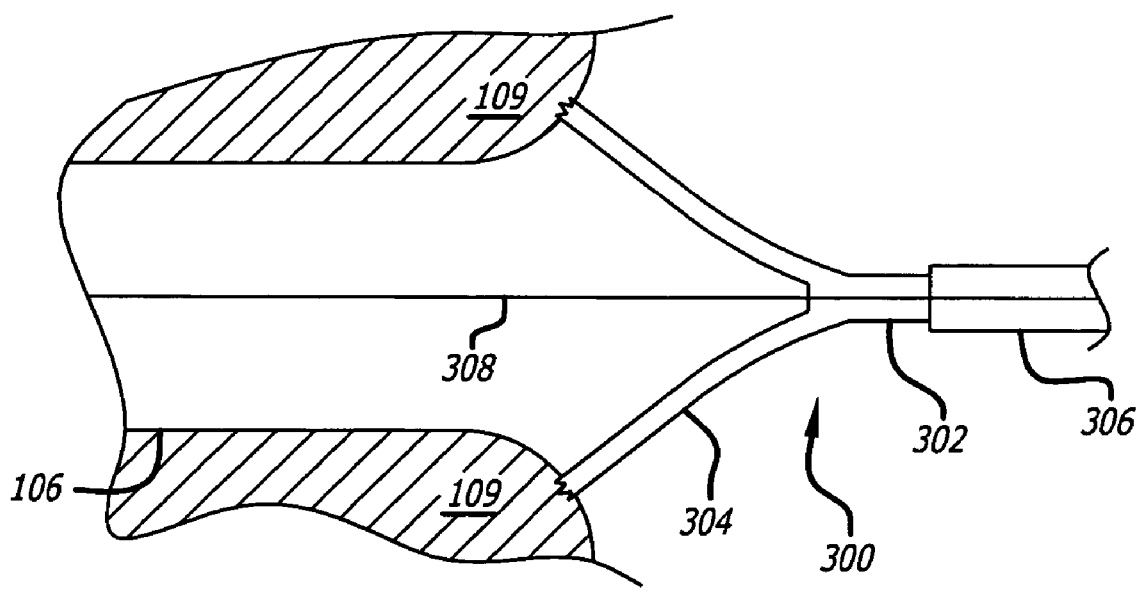
FIG. 17 illustrates a side view of an opposing arm treatment catheter according to the present invention.

Referring now to FIG. 17, a preferred embodiment of a treatment catheter 300 with opposing arms 304 is shown for creating electrical block. The opposing arms 304 are pre-configured to bend away from the axis of catheter body 302 and guide wire 308 to an appropriate diameter which may be defined from a pre-procedure MRI, or other imaging techniques. At the distal tips of opposing arms 304 are one of any number of ablation devices which may be, for example, energy, mechanical, chemical, or other known methods.

The treatment catheter 300 does not require an additional anchoring/guide catheter since the opposing arms 304 are configured to contact the target tissue of the pulmonary ostium 109. However, this treatment catheter 300 may be used with such anchoring/guide catheters, previous examples of which can be seen in this application.

In operation, the treatment catheter 300 operates in much the same manner as other treatment catheters, in that the treatment catheter 300 is positioned within the left atrium, possibly transeptally while the guide wire 308 is directed into the pulmonary vein 106. Next, the sheath 306 is moved in a proximal direction to expose the opposing arms 304, which in turn move away from the axis of the guide wire to a position seen in FIG. 17. The treatment catheter 300 is then advanced distally towards the pulmonary vein 106 until the tips of opposing arms 304 contact the target area of the ostium 109. The treatment arms 304 can be pressed in contact with the tissue around the ostium 109 at the desired points for ablation. It can be seen that they can easily be rotated to ablate additional points. When the procedure is complete, the sheath 306 may be moved in a distal direction relative to the catheter body 302, sliding over the opposing arms 304 and compacting the overall size of the treatment catheter 300 for removal from the body.

While two opposing treatment arms 304 are shown in FIG. 17, additional treatment arms may be included for treating additional targets areas at the same time. Additional treatment arms may also be included as positioning guides to ensure ablation to the proper target tissue area. It is also anticipated that the treatment arms 304 could be configured with only one treatment arm 304 being a treatment arm, while one or more additional arms 304 act as positioning guides.

Figure 20:
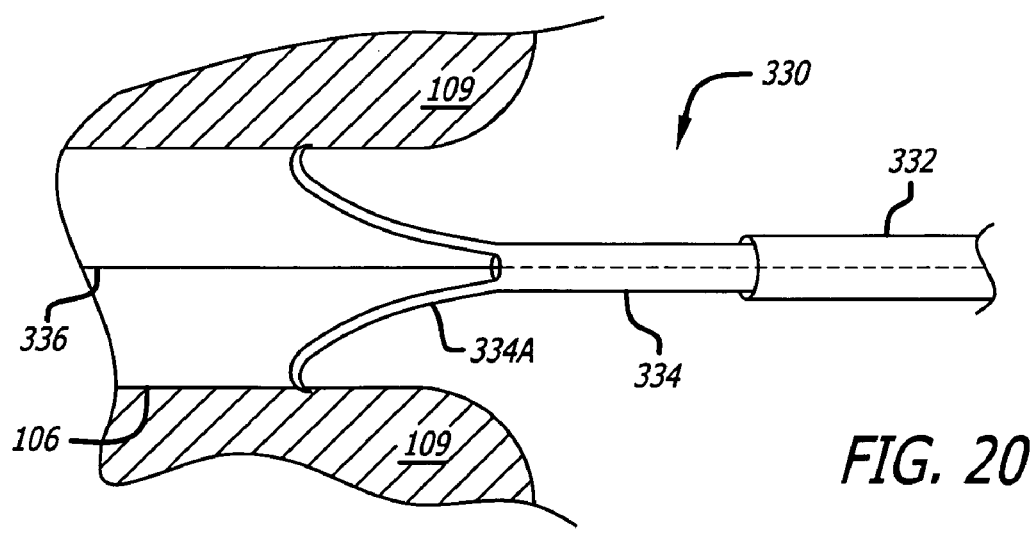
FIG. 20 illustrates a side view of an opposing arm treatment catheter according to the present invention.

Referring to FIG. 20, a similar preferred embodiment is illustrated, having two opposing treatment arms 334a which branch from a catheter body 334. A sheath 332 is pulled back by a user during a procedure to expose the treatment arms 334a that expand away from the axis of the guide wire 336 and catheter body 334. Unlike the embodiment of FIG. 17, the treatment arms 334a have a smaller degree of expansion away from the center axis of the treatment catheter 330, while also having curved ablation tips at the ends of the treatment arms 334a. The smaller expansion angle of the treatment arms 334a allow for position the treatment arms within the pulmonary vein 106 as opposed to around the ostium 109. The curved ablation tips of the treatment arms 334a are angled to contact the walls of the pulmonary vein 106 to cause desired ablation during a procedure. When finished, the user may simply slide the sheath 332 distally to cover the treatment arms 334a, repacking the treatment catheter 330 for removal from the patient.

Figure 18A:
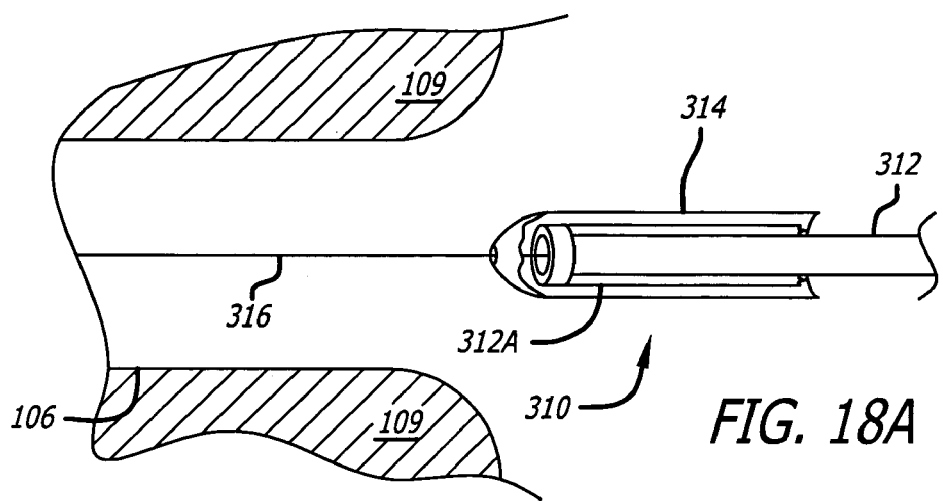
FIG. 18a–18c illustrates a side view of an opposing arm treatment catheter according to the present invention.
Figure 18B:
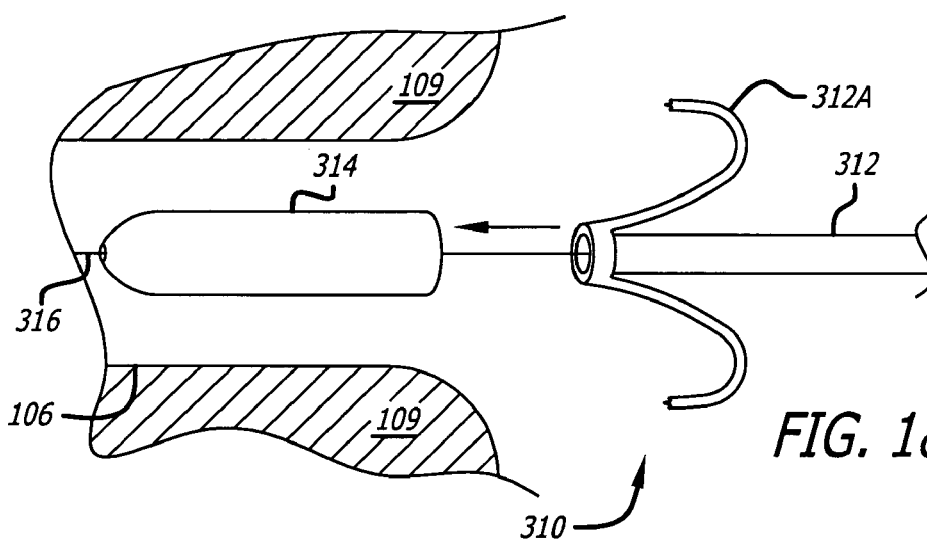
Figure 18C:
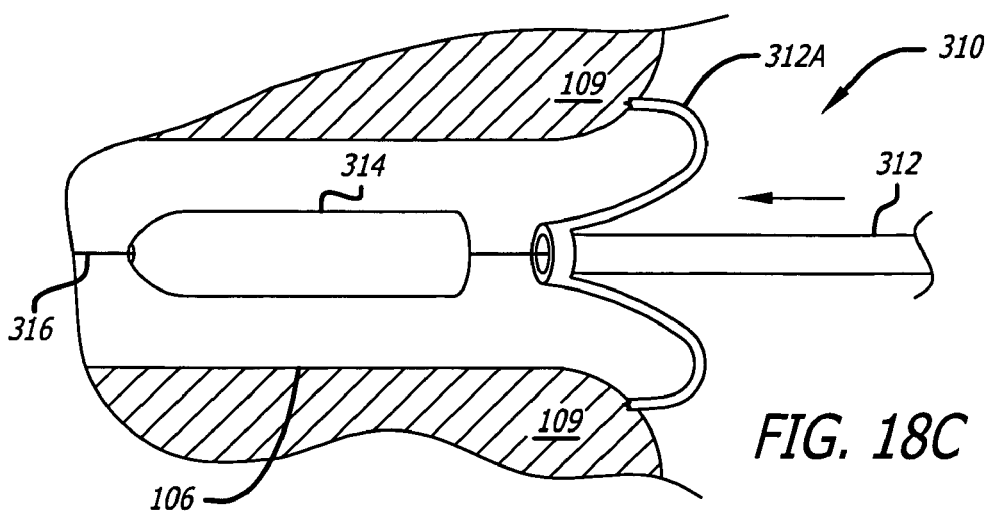

FIGS. 18a-c illustrate another preferred embodiment of a treatment catheter 310 according to the present invention, having backwardly angled treatment arms 312a. Generally, the treatment catheter 310 is similar to the previously described embodiment in FIG. 17, in that the treatment catheter 310 is positioned into the left atrium of a patients heart while a guide wire 316 is directed into the pulmonary vein 106. The treatment catheter 310 differs, however, from previous embodiments due to backwardly angled treatment arms 312a. The sheath 314 is fixed to the guide wire 316, allowing the sheath 314 to move relative to catheter body 312 and treatment arms 312a. The guide wire 316 is positioned through a lumen within the treatment catheter body 312, allowing a user at the proximal end of the catheter 310 to move and manipulate the guide wire 316 and catheter body 312.

As seen in FIG. 18a, the treatment catheter 18a is positioned near the ostium 109 of the pulmonary vein 106. At this time, the treatment arms 312a are deflected within the sheath 314. Next, a user moves the guide wire 316 in a distal direction relative to the catheter body 312, which also moves the sheath 314 away from the catheter body 312, exposing the treatment arms 312a. Finally, the treatment catheter 310 is moved distally toward the pulmonary vein 106 until the ablative tips of treatment arms 312a contact the ostium 109 of the pulmonary vein 106, seen in FIG. 18c. The catheter body 312 may be rotated during the procedure to contact multiple points within a target area. As mentioned above, additional arms 312a may be included for ablating additional target sites at once or to act as guides to ensure proper treatment catheter 310 location.

Figure 19:
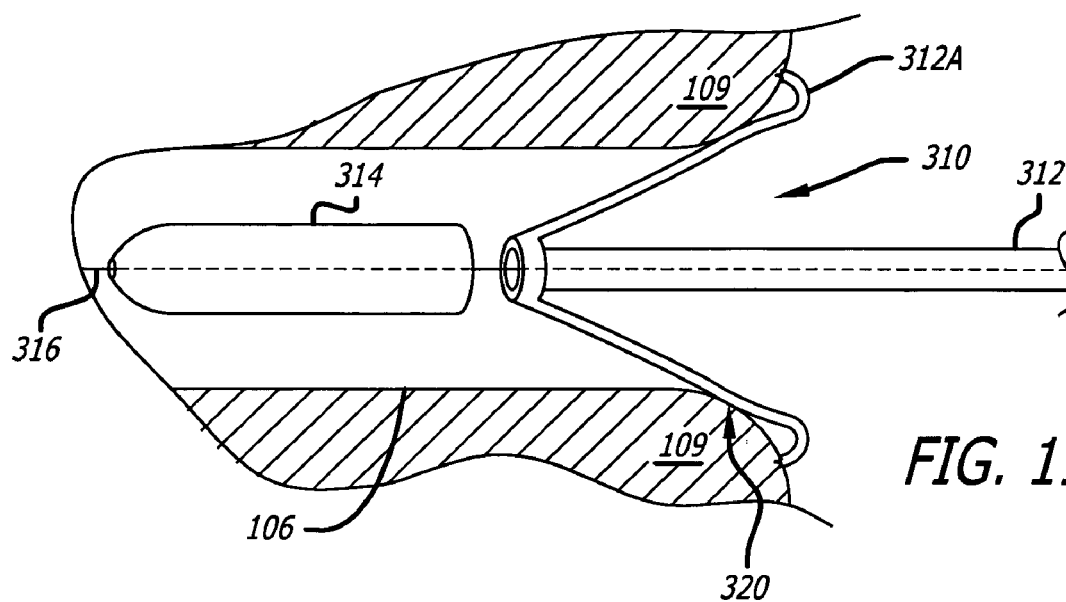
FIG. 19 illustrates a side view of an opposing arm treatment catheter according to the present invention.

FIG. 19 illustrates a preferred embodiment similar to that of FIG. 18a–18c, except for the treatment arms 312a are preconfigured to expand to a wider angle. This wider expansion angle allows the treatment arms 312a to expand until they contact the wall of the pulmonary vein 106, seen at point 320. Thus, a wider range of pulmonary vein 106 diameters can be treated by simply increasing preconfigured expansion angle. This also facilitates treating sites at a known distance around the ostium 109 of the pulmonary vein, defined by the arm 312a length out from the point which presses against the pulmonary vein wall to the treatment tip.

Figure 21A:
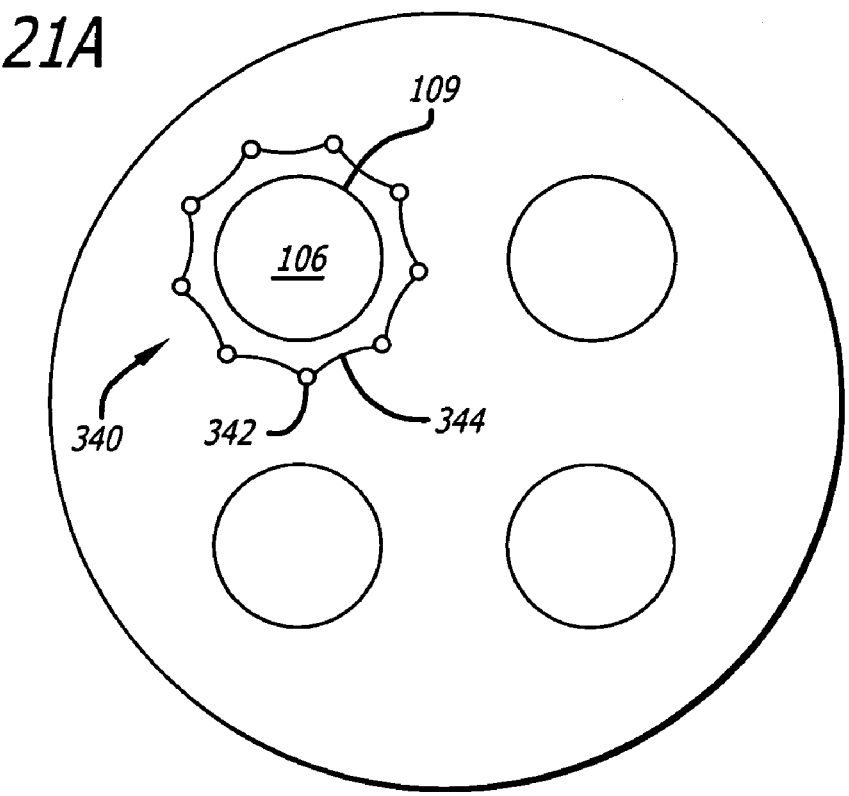
FIG. 21a illustrates a top view of a tethered ablation device according to the present invention.
Figure 21B:
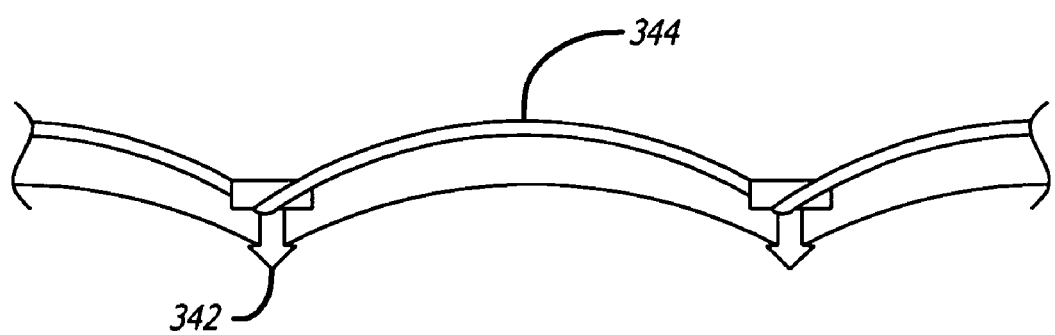
FIG. 21b illustrates a side view of the tethered ablation device of FIG. 21.

In another preferred embodiment seen in FIGS. 21a and 21b, multi-arm treatment catheters (not shown), similar to those seen in the embodiments of FIGS. 17–20, could be used to deploy a series of pins 342 around the ostium 109 of a pulmonary vein 106, which are further connected by a tether 344. Each pin 342 may be deployed by a treatment arm of such a deployment catheter.

The tether 344 is created from a material which causes an additional healing response within the target tissue and can thereby help produce a continuous line of electrical block between the deployed pins. Possible tether 344 material may include biodegradeable polymers such as polyorthoesters or polycaprolactone, engineering polymers such as silicone, or even metals such as copper. Further examples and details can be seen in commonly assigned U.S. Provisional Application No. 60/467,298 entitled Methods and Devices for Creating Electrical Block at Specific Targeted Sites in Cardiac Tissue, which is hereby incorporated by reference.

Expandable Linear Ablation Positioning Devices

Figure 22A:
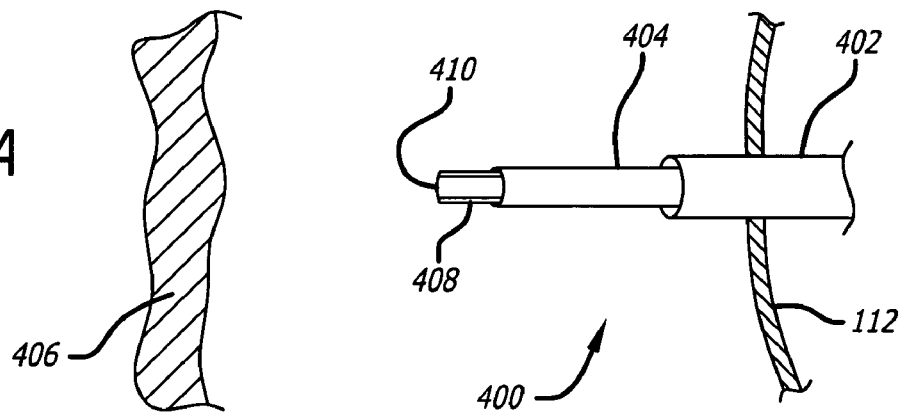
FIG. 22a–22c illustrates side views of an expandable linear ablation device according to the present invention.
Figure 22B:
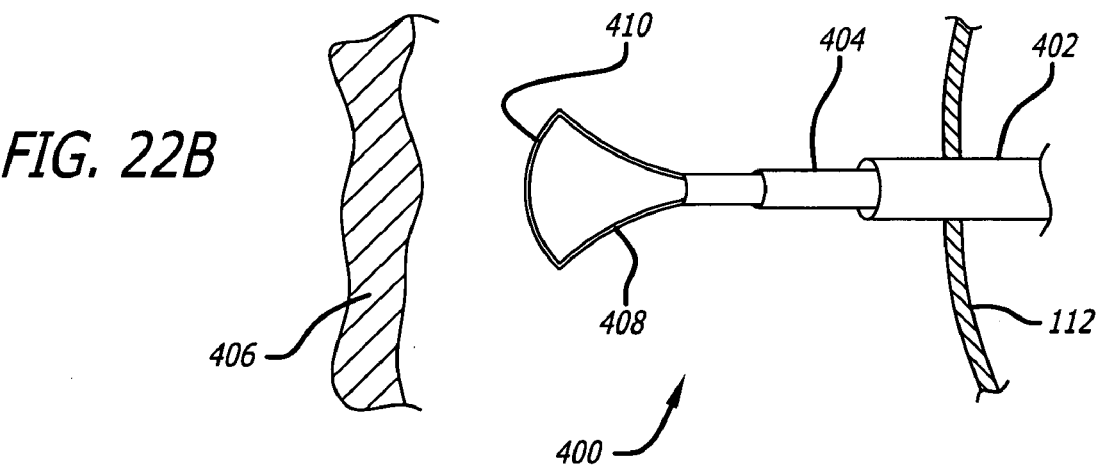
Figure 22C:
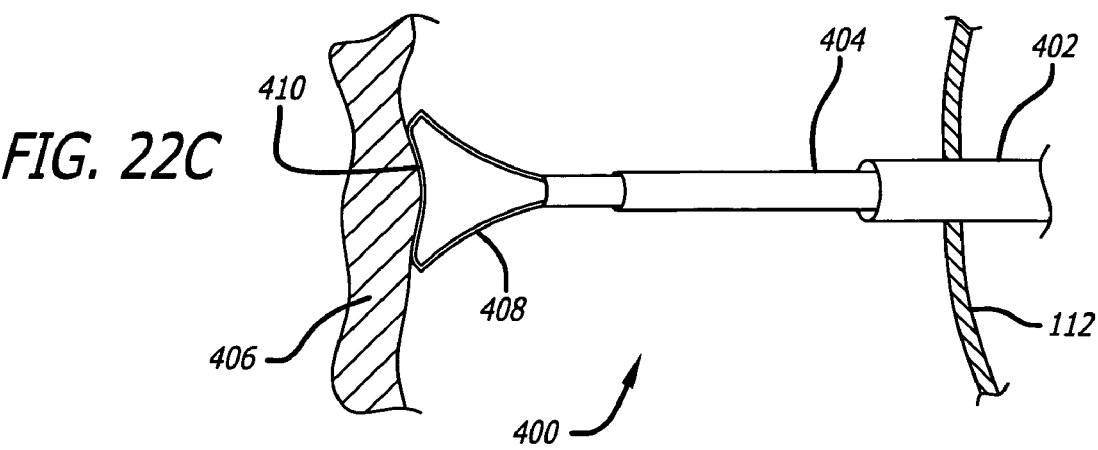

Referring now to FIGS. 22a–22c, a preferred embodiment of an expandable linear positioning and ablation device 400 is illustrated, having a conforming electrode 410 positioned by two retractable electrode arms 408. The conforming electrode 410 is composed of a linear, flexible material which allows the expandable positioning and ablation device 400 to conform to irregular tissue shapes 406 and create a linear ablation pattern.

FIG. 22a shows the linear positioning and ablation device 400 in a retracted state, with conforming electrode 410 and retractable electrode arms 408 retracted within constraint sheath 404. As with previous embodiments, the expandable linear positioning and ablation device 400 is delivered to the left atrium transeptally, via transeptal sheath 402 through the septum 112.

FIG. 22b illustrates the linear positioning and ablation device 400 in a fully extended position, with retractable electrode arms 408 extended and angled away from the central axis of the linear positioning and ablation device 400 so as to spread apart the conforming electrode 410 to a generally linear shape.

FIG. 22c shows the linear ablation device 400 pressed against irregular tissue 406, allowing the conforming electrode 410 to conform to the irregular shape of the tissue 406 to create a linear ablation.

Figure 26A:
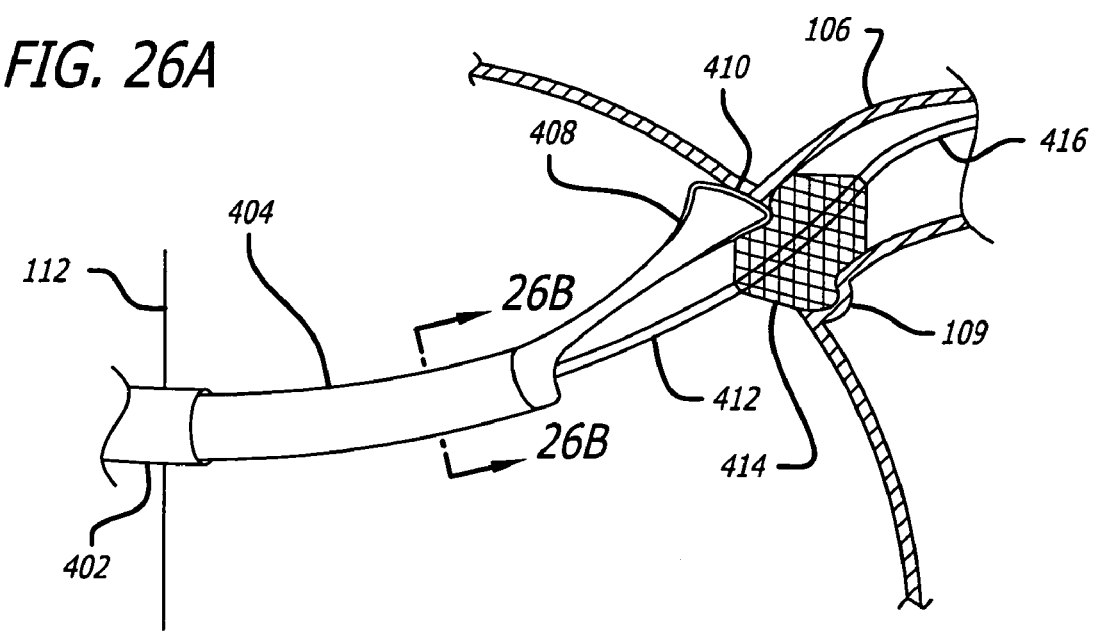
FIG. 26a illustrate a side view of an expandable linear ablation device according to the present invention.
Figure 26B:
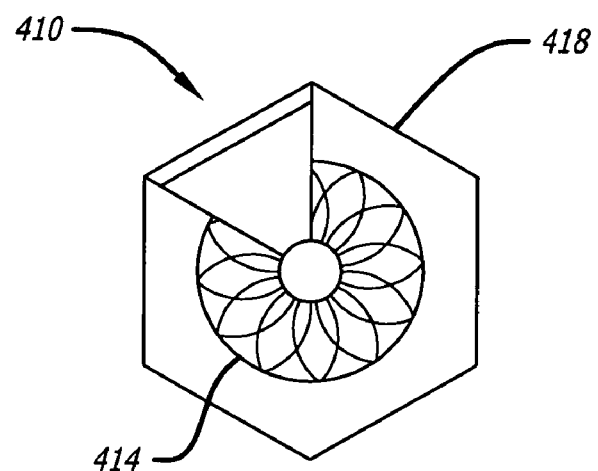

Although the linear positioning and ablation device 400 may be used alone, without further guiding devices, the linear positioning and ablation device 400 may also be used in conjunction with an anchoring or guiding catheter, examples of which have been previously disclosed in this application. For example, FIGS. 26a and 26b illustrate the linear positioning and ablation device 400 in a deployed state with a mesh anchoring catheter 412, similar to those described in FIGS. 10–16.

In operation, the linear ablation device 400 is deployed in a manner described in FIGS. 22a–22c. Next, referring to FIGS. 26A and 26B, a user rotates the linear positioning and ablation device 400 around the expanded mesh section 414, occasionally pressing the conforming electrode 410 against the irregular tissue of the ostium 109. In this manner, a linear ablation pattern 418 (seen in FIG. 26B) is formed, creating a continuous pattern of electrical block around the pulmonary vein 106.

Figure 23A:
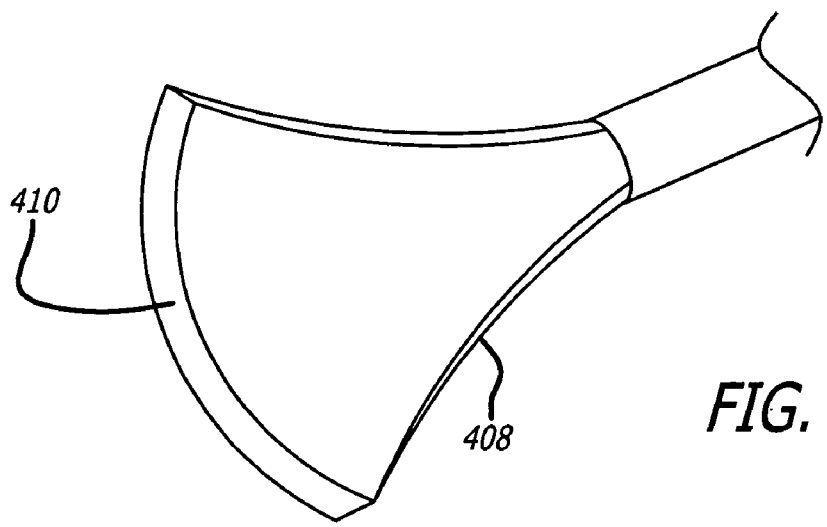
FIG. 23a illustrates a side view of an expandable linear ablation device according to the present invention.
Figure 23B:
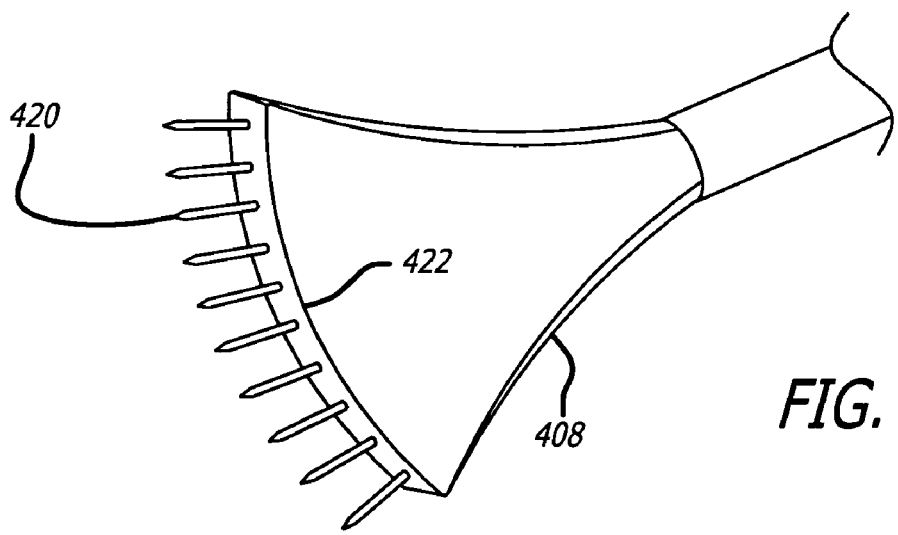
FIG. 23b illustrates a side view of an expandable linear ablation device according to the present invention.
Figure 23C:
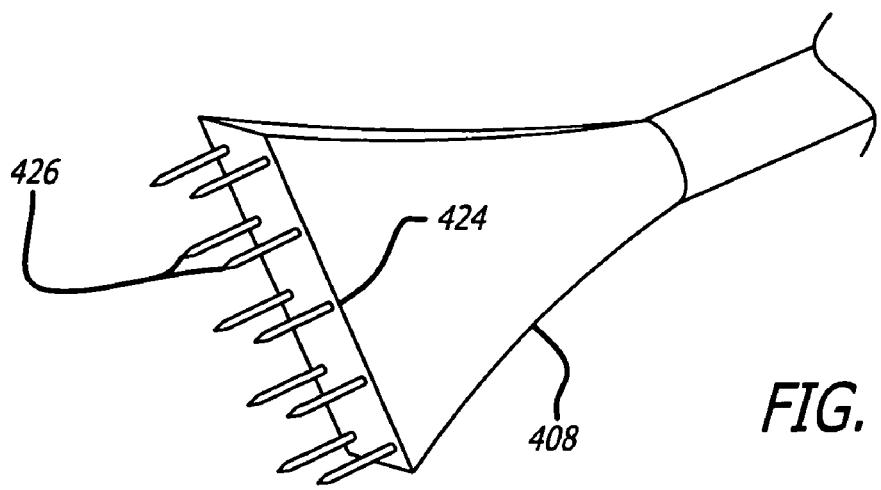
FIG. 23c illustrates a side view of an expandable linear ablation device according to the present invention.
Figure 24A:
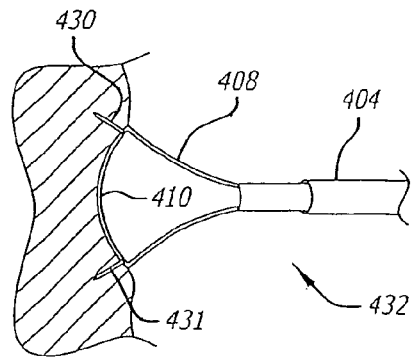
FIGS. 24a–24d illustrate a side view of an expandable linear ablation device according to the present invention.
Figure 24B:
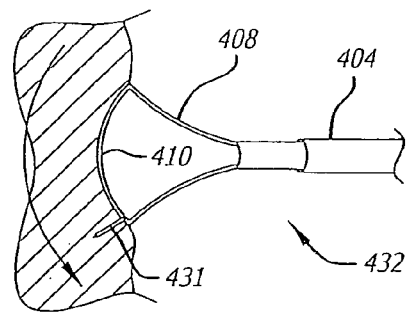
Figure 24C:
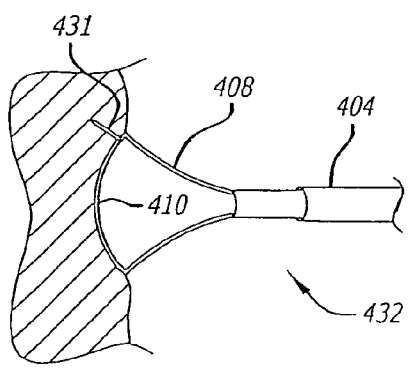
Figure 24D:
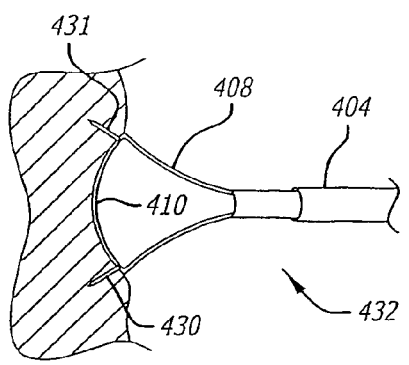

FIGS. 23a–23c illustrate three different embodiments of the electrode of the linear positioning and ablation device 400. FIG. 23a shows a magnified view of the previously described conforming electrode 410, which provides ablation energy, such as radio frequency (RF), to target ablation tissue.

FIG. 23b provides a preferred alternative embodiment of the linear positioning and ablation device 400 having monopolar ablation electrode needles 420 mounted on a conforming backing 422. The ablation needles may use a variety of ablation energies, such as RF, ultrasound, or microwave energy. The conforming backing 422 allows the monopolar ablation needles to conform to irregular tissue shapes while also providing the benefits of providing the ablation energy deeper into the tissue, creating a more uniform ablation through the depth of the tissue.

FIG. 23c is similar in shape to the previous figure, but instead utilizes bipolar ablation needles 426 to create an ablation line on irregular target tissue. To help fit such irregular target tissue shapes, the bipolar ablation needles 426 are fixed to a conforming backing 422, providing additional movement and flexibility between ablation needles 426. As with 23a and 23b, the present embodiment may use RF, ultrasound, or microwave energy to create a bipolar ablation line. In this embodiment, the bipolar ablation needles 426 are configured in two rows. These rows have opposite polarity during ablation so that only the tissue between the rows are ablated. Further details may be seen in U.S. Provisional Application No. 60/514,428, filed Oct. 24, 2003, entitled Methods And Devices For Creating Electrical Block At Specific Sites In Cardiac Tissue With Targeted Tissue Ablation, hereby incorporated by reference.

FIGS. 24a–24d illustrate another preferred embodiment of the linear positioning and ablation device 432 having retractable anchoring pins 430, 431 for maneuvering the linear positioning and ablation device into a desired ablating location. The linear positioning and ablation device 432 is first moved into a desired initial ablation position using conventional techniques described above. Next, anchoring needles 430 and 431 are advanced into the target tissue to hold the position for ablation. After ablating this location, anchoring needle 430 is retracted, allowing the linear ablation device 432 to pivot on anchoring needle 431 to a next desired position of ablation. Anchoring needle 430 will then be anchored into a new position and the ablation may be performed on the second target area. In this manner, a continuous line of ablation is created by "walking" the linear ablation catheter.

Figure 25A:
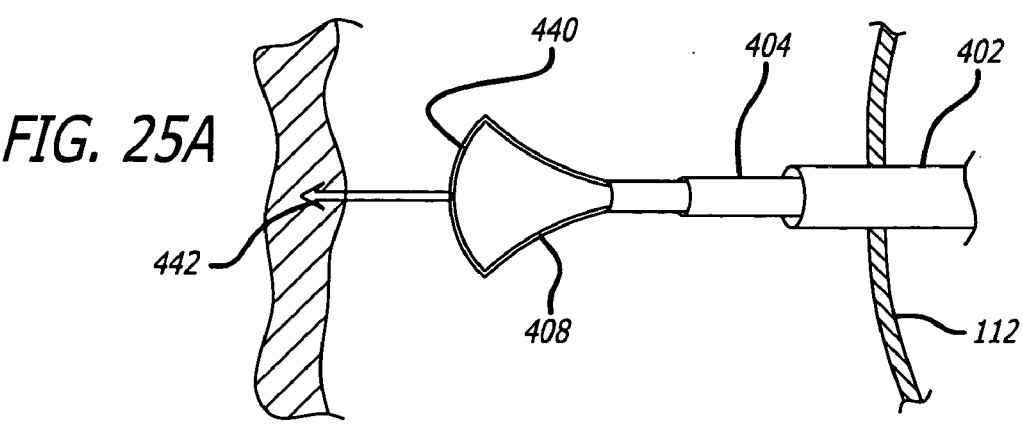
FIG. 25a illustrate a side view of an expandable linear ablation device according to the present invention.
Figure 25B:
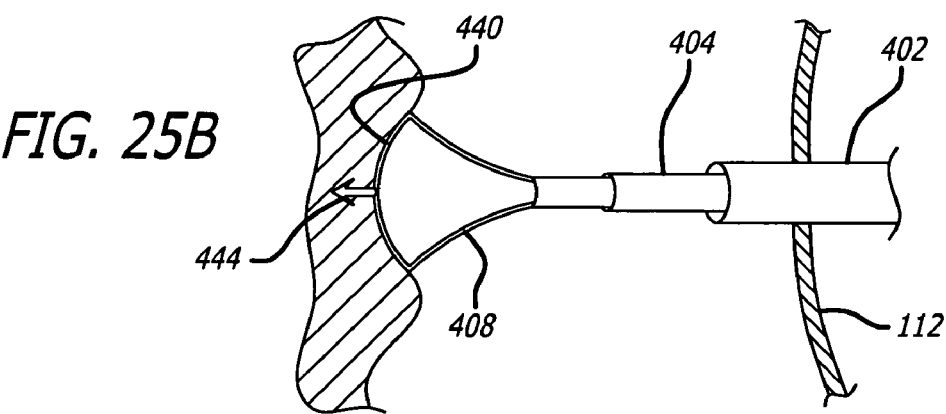
FIG. 25b illustrate a side view of an expandable linear ablation device according. to the present invention.

Single removable anchoring needles 442 or 444 may also be located at the center of conforming electrode 440, as seen in FIGS. 25a and 25b. FIG. 25a shows an elongated anchoring needle 442, while FIG. 25b shows a smaller anchoring needle 444. Both anchoring needle designs 442, 444 are presented for maintaining the desired position of conforming electrode 440, which ensure the ablative procedure is performed at a desired location.

Many different designs of anchoring needles may be used for the preferred embodiments of the linear ablation devices seen in FIGS. 25a–25b. Indeed, for any ablation devices where it is desired to provide an anchoring capability, there are many different concepts for anchoring needles. A few exemplary designs of such removable anchoring needles can be seen in FIGS. 27a–27e.

Figure 27A:
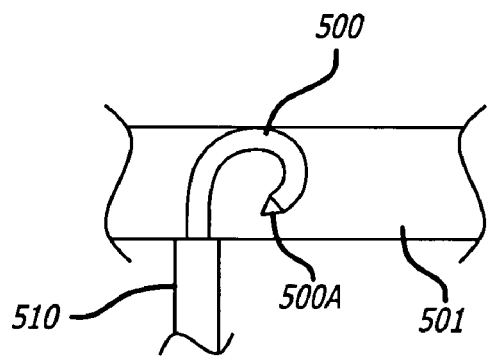

FIG. 27a shows a curved anchoring needle 500 composed of an elastic material such as nitinol, having a pointed tip 500a. The anchoring needle 500 is held straight in a delivery sheath 510 due to the stiffness of the delivery sheath 510 but regains its natural curved shape as it is advanced out the end of the sheath 510. In this way it forms a loop through the target tissue 501, providing anchoring support. The anchoring needle 500 can be reversed by drawing the needle back into the sheath 510. The anchoring needle 500 for such a system would be preferable to be small enough in cross section that it would not produce a big enough hole in the wall of the tissue 501 to cause bleeding if it pierced through the entire wall thickness.

Figure 27B:
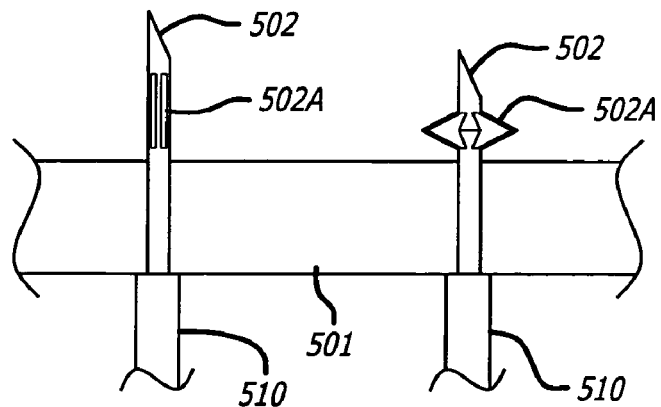

FIG. 27b shows another embodiment of an anchoring needle 502 which functions like a rivet. This anchoring needle 502 is also preferably composed of an elastic material such as nitinol. In this embodiment, the tip of the anchoring needle 502 is advanced out of the sheath 510 and pierces the target tissue. A needle segment 502a immediately behind the sharp tip has a preformed shape which flares out to a much bigger diameter. This segment expands as it passes through the tissue of the wall, anchoring the needle 502 in the tissue 501.

Figure 27C:
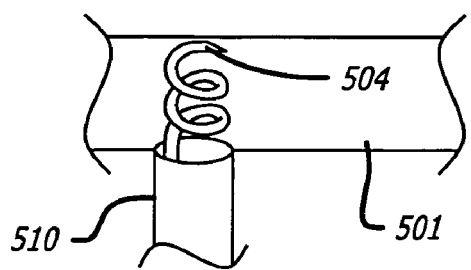

FIG. 27c shows an anchor needle embodiment which uses a helical needle which can be screwed into the tissue to anchor and unscrewed to release.

Figure 27D:
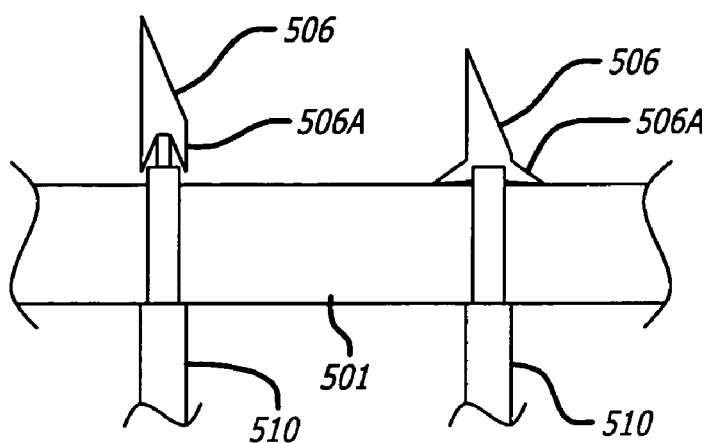

FIG. 27d illustrates a barbed needle 506 which functions like an umbrella. The barb's 506a natural position is tight against the central shaft. These barbs 506a are splayed out elastically by a sheath 510 which is advanced forward. The barbs 506a return to their original position when the sheath 510 is pulled back.

Figure 27E:
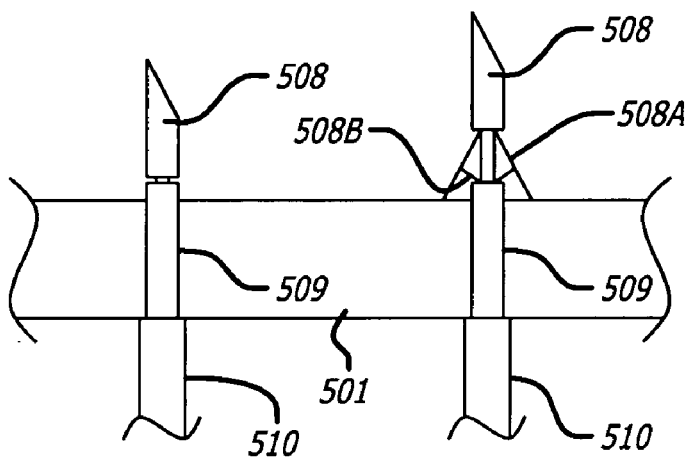

FIG. 27e illustrates yet another embodiment of a barbed anchoring needle 508, having barbs 508a formed so their natural position is in a flared out conformation. The barbs 508a are constrained by a sheath 509 while piercing the tissue and the sheath is then advanced to release the barbs 508a. The barbs 508a have arms 508b which branch off and angle back into the end of sheath 509. Theses arms 508b act to collapse the barbs 508a when the sheath is advanced. To withdraw the anchoring needle 508, the insertion steps are simply reversed.

Figure 28:
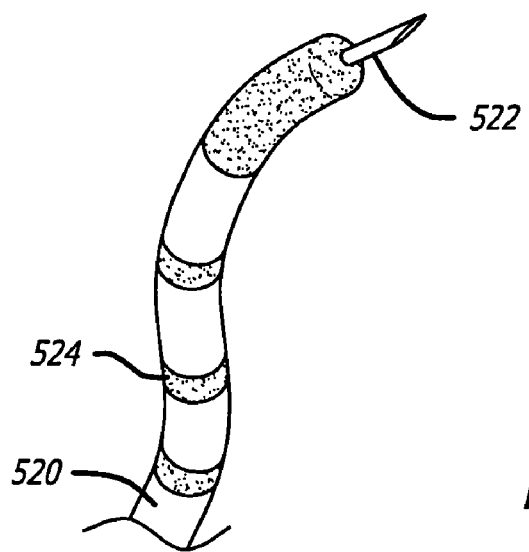

FIG. 28 illustrates an ablation catheter 520 with additional electrodes 524, as is commonly used today, but having a retractable anchoring needle 522 protruding from its tip. The anchoring needles serves to better position the ablation catheter 520 in place.

The retractable anchoring needle 522 may include one of the previously mentioned needle designs in FIGS. 27A–27E, or other retractable needle designs. In addition to acting as an anchor, the retractable anchoring needle 522 may also serve as an ablation electrode, yielding deeper ablation with less energy. The ablation catheter 520 may alternatively serve to anchor and guide, while a user provides a separate ablation catheter, similar to those seen in FIG. 11–15 where the treatment arm rotates around the perimeter of the ostium.

Although the invention has been described in terms of particular embodiments and applications, one of ordinary skill in the art, in light of this teaching, can generate additional embodiments and modifications without departing from the spirit of or exceeding the scope of the claimed invention. Accordingly, it is to be understood that the drawings and descriptions herein are proffered by way of example to facilitate comprehension of the invention and should not be construed to limit the scope thereof.

What is claimed is:

1. A method of positioning an ablation device within a body comprising:
    providing an ablation tool having an elongated body and a flexible electrode disposed between at least two arm members on a distal end of said ablation tool, said flexible electrode being more flexible than said at least two arm members:
    directing said distal end of said ablation tool to a target tissue area within said body;
    expanding said flexible electrode;
    contacting said flexible electrode to substantially conform to a surface of said target tissue area;
    ablating at least a surface of said target tissue area;
    pivoting one end of said flexible electrode around an opposite end of said flexible electrode;
    contacting said flexible electrode to a new surface of said target tissue area;
    ablating said new surface of said target tissue.

2. The method of claim 1, further comprising a repetition of said pivoting, said contacting and said ablating until said target tissue is fully ablated.

3. The method of claim 1, wherein said opposite end of said flexible electrode is fixated in said target tissue with a needle during said pivoting.

4. The method of claim 1, wherein prior to said pivoting, a needle in said opposite end of said flexible electrode is extended to penetrate said target tissue and thereby stabilize said opposite end of said flexible electrode.

5. The method of claim 1, wherein prior to said pivoting, both said end and said opposite end of said flexible electrode are stabilized in said target tissue with a needle.

* * * * *